United States Patent [19]
Danielson et al.

[11] Patent Number: 4,926,489
[45] Date of Patent: May 15, 1990

[54] RETICLE INSPECTION SYSTEM

[75] Inventors: Donald L. Danielson, Palo Alto; Mark J. Wihl, Tracy; David A. Joseph, Santa Cruz, all of Calif.

[73] Assignee: KLA Instruments Corporation, Santa Clara, Calif.

[21] Appl. No.: 104,740

[22] Filed: Oct. 5, 1987

Related U.S. Application Data

[63] Continuation-in-part of Ser. No. 891,638, Aug. 1, 1986, which is a continuation of Ser. No. 474,461, Mar. 11, 1983, abandoned.

[51] Int. Cl.$^5$ .............................................. G06K 9/00
[52] U.S. Cl. ........................................ 382/8; 382/34; 356/399
[58] Field of Search ............... 356/390, 394, 398, 399, 356/400, 401; 358/106, 107; 382/8, 30, 34

[56] References Cited
U.S. PATENT DOCUMENTS

| | | | |
|---|---|---|---|
| 3,909,602 | 9/1975 | Micka | 356/394 |
| 4,213,117 | 7/1980 | Kembo et al. | 382/8 |
| 4,240,750 | 12/1980 | Kurtz et al. | 356/394 |
| 4,247,203 | 1/1981 | Levy et al. | 356/390 |
| 4,301,443 | 11/1981 | Sternberg et al. | 382/27 |
| 4,334,241 | 6/1982 | Kashioka et al. | 382/8 |
| 4,441,207 | 4/1984 | Lougheed et al. | 382/41 |

Primary Examiner—Leo H. Boudreau
Assistant Examiner—Jose L. Couso
Attorney, Agent, or Firm—Rosenblum, Parish & Bacigalupi

[57] ABSTRACT

An automatic inspection system including an illuminator for illuminating a reticle or photomask to be inspected, while optically projecting a magnified image of the reticle or photomask onto a plurality of detector elements. A carriage assembly moves the object at a constant velocity to allow the detector elements to sequentially view the entire surface to be inspected. The detector elements are responsive to the intensity of light incident thereupon and are periodically scanned to obtain a two-dimensional measured representation of the object. A database adaptor formulates a two-dimensional representation from the design database description corresponding to the scanned object simultaneously and in synchronism with the scanning of the photomask or reticle. The measured and database adapted representation of the scanned object are input to a signal processor for alignment and defect detection. While the representations are shifted through a memory, an alignment circuit dynamically measures and corrects for misalignment between the representations, so that a defect detector can effectively compare the representations for defects. Additional correction of misalignment between the representations is obtained by modulating the size of the measured representation as detected by the detector elements. At the operator's option, a second measured image of a multi-cell reticle or photomask may be used for comparison as a substitute for the database representation.

42 Claims, 13 Drawing Sheets

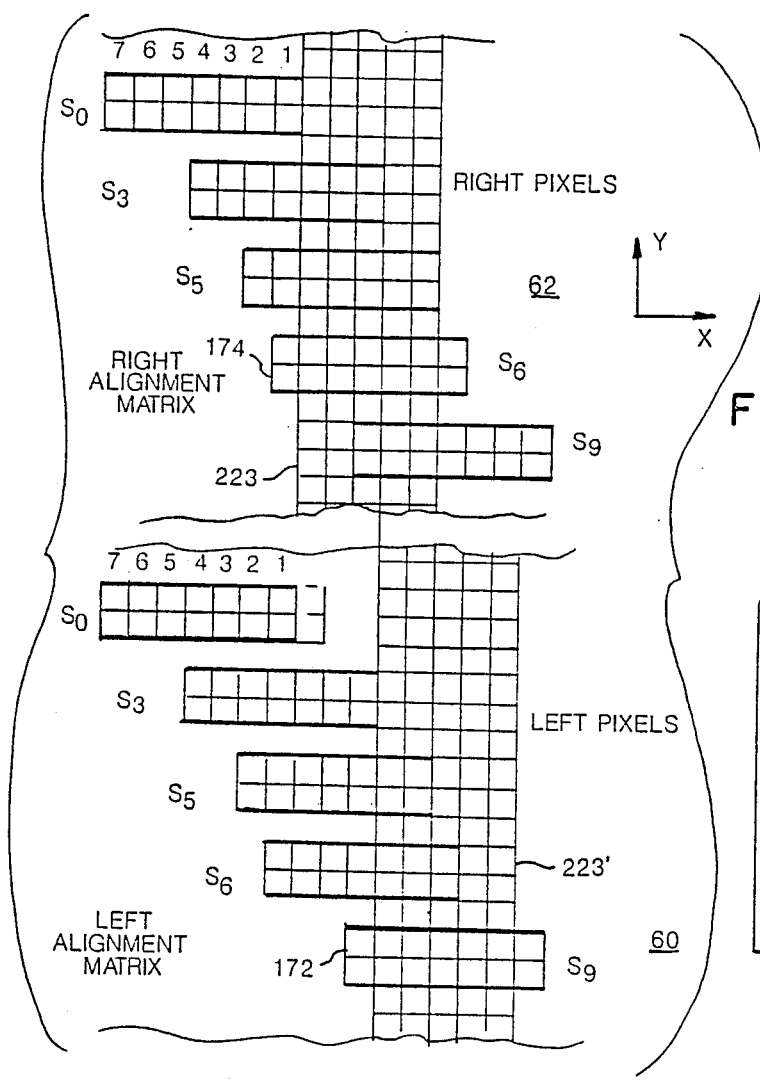
FIG. 12
FIG. 13
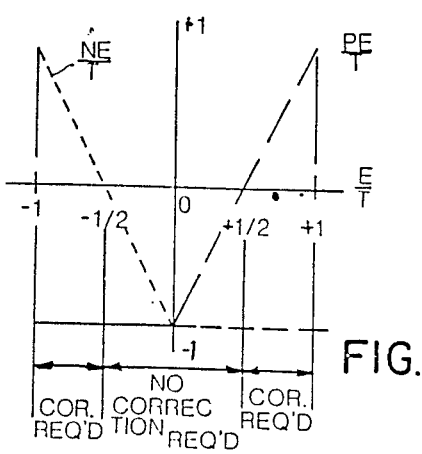
FIG. 14

RETICLE INSPECTION SYSTEM

This application is a continuation-in-part of U.S. patent application Ser. No. 891,638 filed Aug. 1, 1986, which is a continuation of Ser. No. 474,461 filed Mar. 11, 1983 (now abandoned).

BACKGROUND OF THE INVENTION

A. Field of the Invention

This invention relates to object inspection apparatus, and more particularly, to an automatic reticle inspection system which utilizes an advanced alignment technique capable of detecting defects in VLSI reticles by comparison to a stored database.

B. Description of the Prior Art

Automatic object inspection systems that use an object comparison fault detection technique have been described in the literature for some time and have been commercially available for a number of years. The technique generally involves scanning the object to be inspected with an electro-optical or other pick-up device and developing an image-like (bit-map) electronic representation of the object so a comparison to a known good electronic representation (bit-map or database) can be made. The known good electronic representation can be obtained by simultaneously scanning a known good object in synchronism with the scanning of the object of unknown quality to develop the bit-map, or by using a previously stored electronic representation (either bit-map or database) of a known good object.

In both of the above comparison techniques, the fault detection method consists of locating differences between the compared objects. To accurately determine faults, the system must register or align the two objects, or electronic representations of the objects, prior to comparison, so that differences caused by actual faults, as opposed to differences merely caused by misregistration, can be detected. Accordingly, the quality of the registration in these systems limits the overall performance or sensitivity of the system to actual faults, that is, the system cannot be so sensitive that it detects misregistration errors. Similarly, the ability of the system to detect very small faults is also determined by the spatial resolution of the pick-up method. In other words, to detect very small faults, the spatial resolution of the system must be very high.

In practice, systems with high spatial resolution, which are used to inspect objects occupying a large surface area, must process data at high speeds in order to complete the inspection in a reasonable and practical amount of time because of the large volume of data. Furthermore, such high spatial resolution systems are more likely to be affected by misregistration errors caused by the mechanical nature of the pick-up device; small differences in spatial distortion, vibration, rotation, displacement, thermal effects, and similar problems can result in significant misregistration errors when the two objects are compared. Such misregistration errors must be controlled or compensated for in order for a system to provide high performance.

In the integrated circuit inspection system described by Micka U.S. Pat. No. 3,909,602, an optical scanner with a 2.5 micron spot size is used to scan a typical chip, having 0.2 inch by 0.2 inch surface dimensions. The unknown device is scanned and the resulting signal is compared with a known good signal. The known good signal is either generated by simultaneously scanning a known good device, or by replaying a stored representation which has been previously obtained by scanning a known good device. Creating a stored representation such as is taught in Micka, would typically require $4 \times 10^6$ data words and would typically require reading at a rate of less than 600 KHZ. Micka suggests that this apparatus may be used to inspect some devices or photomasks.

Micka teaches a method for finely adjusting the physical position of the device or devices being scanned for the purpose of static registration. Micka points out that a point-by-point comparison would not be satisfactory because of misalignments that might occur. Thus, Micka teaches a comparing system which uses many spots in a neighborhood, with a cross-correlation technique, to provide higher sensitivity than would be obtainable with a simple point-by-point method. One disadvantage to this system is that it depends on static positioning for registration and provides no means by which to dynamically compensate for registration errors, other than providing a detection method which is somewhat resistant to registration errors.

Another disadvantage to this system is that reducing the scanning spot size (such as to 0.5 microns) or scanning objects with larger surfaces (such as $0.5 \times 0.5$ inches) when inspecting VLSI devices, photomasks or reticles can result in a stored data volume requirement greater than $6 \times 10^8$ words, and require a data rate greater than 6 MH$_z$, just to complete the inspection in a reasonable amount of time. Achieving this data volume and data rate is not practical with presently available storage media. Hence, the technique described by Micka is not practical for the inspection of VLSI devices. Even common compression methods such as run-length encoding or DPCM will produce only a $2\times$ to $3\times$ compression in this type of application, which still results in excessive data volume.

An additional disadvantage of the apparatus taught by Micka is that the known good device must first be inspected by other means and certified to be good before it can be used as a master. A human operator can inspect larger devices by means of a microscope, but to inspect VLSI devices, with sides as small as 0.5 inches, by such means, would require microscope magnification as high as $1000\times$. At $1000\times$ magnification, each field-of-view would be extremely small, and as many 62,000 fields-of-view would be required to examine the whole device. The use of human operators for such inspections has proven to produce significant operator errors and fatigue.

An alternate approach is to electrically test the device, with certification dependent on the device passing the test. Not all faulty devices will be detected by electrical testing because some process errors do not produce immediate failures. Faulty certification of the master can result in even greater problems when applied to certifying VLSI devices. In order to electrically test devices, the devices must first be fabricated, and then electrically tested. A fabricated device that passes a first time-test may actually be good, but the device could also have a hidden defect that would not be exposed until later. If the device fails, the fault may be due to a photomask or reticle fault, or some other process fault. When a device fails, there may be no way to determine which is the actual cause. This method of certification is poor at best and results in a considerable waste of time and money. Thus, the inability to accurately certify a VLSI device prior to usage of the Micka apparatus proves to be a significant disadvantage.

A solution to this problem was offered by Kryger, U.S. Pat. No. 4,218,142, wherein an apparatus is described in very general terms which compares an unknown photomask to an electronic representation stored in a high-speed memory device. However, in Kryger, the memory device only stores a small portion of the total electronic representation and must be successively reloaded by the computer with the next section after each applicable portion of photomask has been inspected. A disadvantage to this approach is that a significant amount of time must be spent reloading the memory device from the relatively slow computer. The time disadvantage would be particularly acute when inspecting single-die or multi-die reticles where few repetitions of the die pattern exist, and where large die and small pixel sizes must be used, resulting in a very large data base size, such as $6 \times 10^8$ words. Thus the Kryger technique apparently provides a slow and inefficient process for inspecting VSLI photomasks and reticles.

The object inspection apparatus described by Lloyd et al, U.S. Pat. No. 3,916,439, uses a TV camera, as the optical pickup device, to compare the TV image of the unknown device with a previously stored image from a known good device. The comparison technique uses the point-by-point method, and the synchronization technique uses line-by-line timing of the TV camera to obtain corresponding data from the storage device. One disadvantage of this type of system is that the synchronization method, comparison method and storage method are not practical for high resolution large area applications like VLSI photomasks and reticles, for many of the same reasons discussed above.

The object inspection apparatus described by Kurtz et al, U.S. Pat. No. 4,240,750, uses a laser scanner as the optical pick-up method for the purpose of inspecting printed circuit parameters. In one embodiment, the apparatus measures the angular position of a lead wire and then compares that position with a desired position. This technique is not applicable to the type of inspection discussed herein. A second embodiment is similar to the type of object inspection techniques described by Applicant. In this embodiment, the printed circuit board to be inspected is scanned with a rectangular raster type sweep with a spot size of about 1.5 mils (37 microns) and a typical area of $3 \times 3$ inches, resulting in about $4 \times 10^6$ data points.

The known good board is first scanned and the resulting electronic representation is stored in a memory. An unknown board is then scanned while simultaneously comparing the electronic representation with the stored representation. Faults are located by performing a point-by-point comparison of the two electronic representations. The synchronization method applied merely consists of the scanner position and memory being addressed from the same counter. Thus, registration is statically accomplished by insuring that the unknown board is positioned in the same position as the known good board, when it was scanned. The disadvantages to this system, when extended to the inspection of VLSI photomasks or reticles, are the same as those mentioned in the previous paragraphs regarding the Micka apparatus.

The object inspection apparatus described by Levy et al, U.S. Pat. Nos. 4,247,203 and 4,347,001, is used for the inspection of photomasks used in the manufacture of semi-conductor devices. These apparatus locate faults in the photomask by simultaneously comparing adjacent die on the photomask and locating differences. Because a known good die is not used in this type of inspection, only random faults can be located, thereby leaving repeating faults still present. Furthermore, Levy states that no storage method is included, due to the large data volume that would be required.

The apparatus described in Levy is designed to be capable of locating 1.25 micron faults. Levy disclose that the mechanical tolerances of such a high sensitivity inspection system, imperfections in the photomask, and operator misalignment of the photomask to be tested can cause the scanned images to be slightly misaligned. This misalignment changes with time during the inspection and with the position of the mask. Unless the misalignment can be compensated for or predicted, defects smaller than the misalignment cannot be detected.

In order to correct any misalignment, Levy discloses an alignment method consisting of a high-speed memory, which can be used to delay the electronic representations from the two die being compared relative to each other to effect a dynamic change in the registration, and a dynamic alignment error detection method, to determine when a registration change needs to be made. Since the objects to be inspected are located on the same plate, many of the misregistration error sources are common to the detection system, and affect both die, such as stage vibration, stage velocity changes, plate rotation, etc. There are also additional error sources which are not common to both die, such as relative vibration of the two optical pick-up units (objectives) or die run-out present on the plate.

The alignment method taught by Levy uses patterns within the die for error information and is capable of dynamically detecting and correcting $\pm 1$ pixel of misalignment over a total range of $\pm 8$ pixels. However, the method is limited to only slow moving misalignments. In addition, as is stated in the disclosure, the alignment method cannot maintain proper alignment when there is no pattern information on the plate for large distances, or if there are sudden changes in registration as might be encountered with a stepping error on a particular die. The overall sensitivity of the apparatus is preserved by the inclusion of a detection method which can, to some extent, tolerate the above mentioned situations, as might be encountered on photomasks.

One disadvantage to the system taught by Levy is that there is no means for locating repeating defects or for inspecting single die reticles since there is nothing to compare against. With the exception of Kryger, in all previously mentioned prior art, a known good stored representation must already exist for there to be anything for the system to use for comparison. Combining any of the stored data methods taught by Micka, Kurtz, or Lloyd, and even that taught by Kryger, to the apparatus taught by Levy would require substantial redesign of the combined systems which is neither suggested nor taught by any of the references. Such a combination would not be able to accommodate the high data volume (as described earlier) and the even higher data rate requirements (as high as 20 MHz) of a system analogous to the present inventions. Furthermore, even if it were possible to produce the stored representation at the required data rate, the alignment method taught by Levy would be far too inadequate to maintain proper alignment between the stored representation and the object being scanned.

The alignment system taught by Levy cannot be effectively extended to make a comparison of a photomask or reticle with a stored representation. Such a use would not be possible because the resulting misalignment errors that would exist would be too great in number, and all of the errors that the two die formerly had in common, such as stage velocity errors, stage vibration, optical pick-up vibration, rotation, and thermal expansion, would only be applicable to the unknown die. Thus, the alignment system would not only have insufficient error detection capability, but would also have insufficient responsiveness.

In addition, since 5× and 10× reticles, or the like, have significantly larger patterns than a 1× photomask, large areas of the plate may contain no pattern. When there is no pattern on the plate, the alignment system cannot track the alignment. Thus, when the pattern is again encountered, the alignment error may be beyond the range of the error detection method and the alignment system, and may not have sufficient responsiveness to prevent detection of any faults solely due to misregistration. Furthermore, an extension of the described technique to ±8 pixels would require up to 50 times more computation, thereby making the system too complicated and slow to be practical. Thus, a reticle inspection system using the above described alignment system would have poor sensitivity, due to the inability of the alignment system to maintain proper alignment.

SUMMARY OF THE PRESENT INVENTION

It is therefore a principal object of the present invention to provide a novel, automatic system for the high performance inspection of reticles and photomasks, especially those used in VLSI integrated circuits.

It is another object of the present invention to provide an automatic system for inspecting reticles and photomasks which includes a novel method of comparing the unknown reticle or photomask with the original design database (CAD) of the reticle or photomask.

It is still another object of the present invention to provide a novel method of simultaneously handling the large database, high speeds and high spatial resolution misregistration attendant with VLSI photomask and reticle inspection, in a cost effective manner.

It is a further object of the present invention to provide an automatic system for inspecting reticles and photomasks having timing and control functions that synchronize an original design database representation with the unknown reticle or photomask so that the alignment system can properly align the design database with the unknown reticle or photomask image.

It is still a further object of the present invention to provide an automatic system for inspecting reticles and photomasks where the system timing and control includes a novel method of modulating pixel size in one-dimension to extend the range of the alignment system so that large slow-moving errors can be efficiently compensated.

It is another object of the present invention to provide an automatic system for inspecting reticles and photomasks that can convert an original design database in a manner such that the stored data base can be synchronously compared with the scanned image of an unknown reticle or photomask wherein the comparison can be made at high speed, large databases can be accommodated and the overall process is very efficient.

It is another object of the present invention to provide an automatic system for inspecting reticles and photomasks that has a novel alignment system which can dynamically compensate for registration errors present when comparison of a reticle or photomask is made with an original design database representation, and where spatial resolution of the automatic system is very high and the inspection speed rapid.

It is still another object of the present invention to provide an automatic system for inspecting reticles and photomasks where the alignment system includes a novel 2-dimensional phase detector for the efficient and high-speed detection of alignment errors in excess of ±1 pixel.

It is another object of the present invention to provide an automatic system for inspecting reticles and photomasks where the alignment system includes a novel, adaptive alignment method which can adjust to the responsiveness of the alignment system according to pattern density and exert alignment activity, such that alignment can be properly maintained in the presence of large areas devoid of patterns.

It is another object of the present invention to provide a reticle and photomask inspection system which gives the operator the ability to optionally select a low-resolution, high-speed operation.

These and other objects, which will hereinafter become apparent, are accompanied in accordance with the illustrated preferred embodiment of the present invention by providing an automatic inspection system including carriage means, illumination means, optical means, detector means, database adaptation means, and signal processing means. The illumination means illuminates a reticle or photomask to be inspected, while the optical means projects a magnified image of the reticle or photomask onto the detector means. The carriage means move the reticle or photomask at a constant velocity to allow the detector means to sequentially view the entire surface to be inspected. The detector means are responsive to the intensity of light incident thereupon and are periodically scanned to obtain a two-dimensional measured representation of the reticle or mask. The database adaptation means formulates a comparable two-dimensional representation of the reticle or photomask from the design database description simultaneous with and in synchronism with the scanning of the photomask or reticle. The measured and database adapted representation of the reticle or photomask are input to the signal processing means for alignment and defect detection. While the representations are shifted through a memory, an alignment circuit dynamically measures and corrects for misalignment between the representations, so that a defect detector can effectively compare the representations for defects. Also included are means for modulating the size of the measured representation to additionally correct for misalignment. At the operators option, a second measured image of a multi-cell reticle or photomask may be used for comparison as a substitute for the database representation.

Some of the numerous advantages of the present invention are that it allows the comparison of a photomask or reticle, especially a single die reticle, with the companion design database for the purpose of locating faults; and especially, repeating faults. The present invention also dynamically and accurately aligns the two representations so that an effective defect inspection can be performed.

These and other objects and advantages of the present invention will no doubt become apparent to those skilled in the art after having read the following detailed description of the preferred embodiment which is illustrated in the several figures of the accompanying drawing.

BRIEF DESCRIPTION OF THE DRAWING

FIG. 12 is a diagrammatic representation of the operation of the X alignment detection functional of the alignment error detection circuit of FIG. 8.

FIG. 13 is a logical truth table depicting the method employed by the alignment error detection circuit to determine the sense of X alignment errors.

FIG. 14 is a graphical representation of normalized alignment correction factors as calculated by an alignment processor portion of the alignment error detection circuit of FIG. 8.

FIG. 15a depicts the operation of an error test computational branch, and FIG. 15b depicts the operation of an accumulator update branch.

DESCRIPTION OF THE PREFERRED EMBODIMENT

Figure 1:
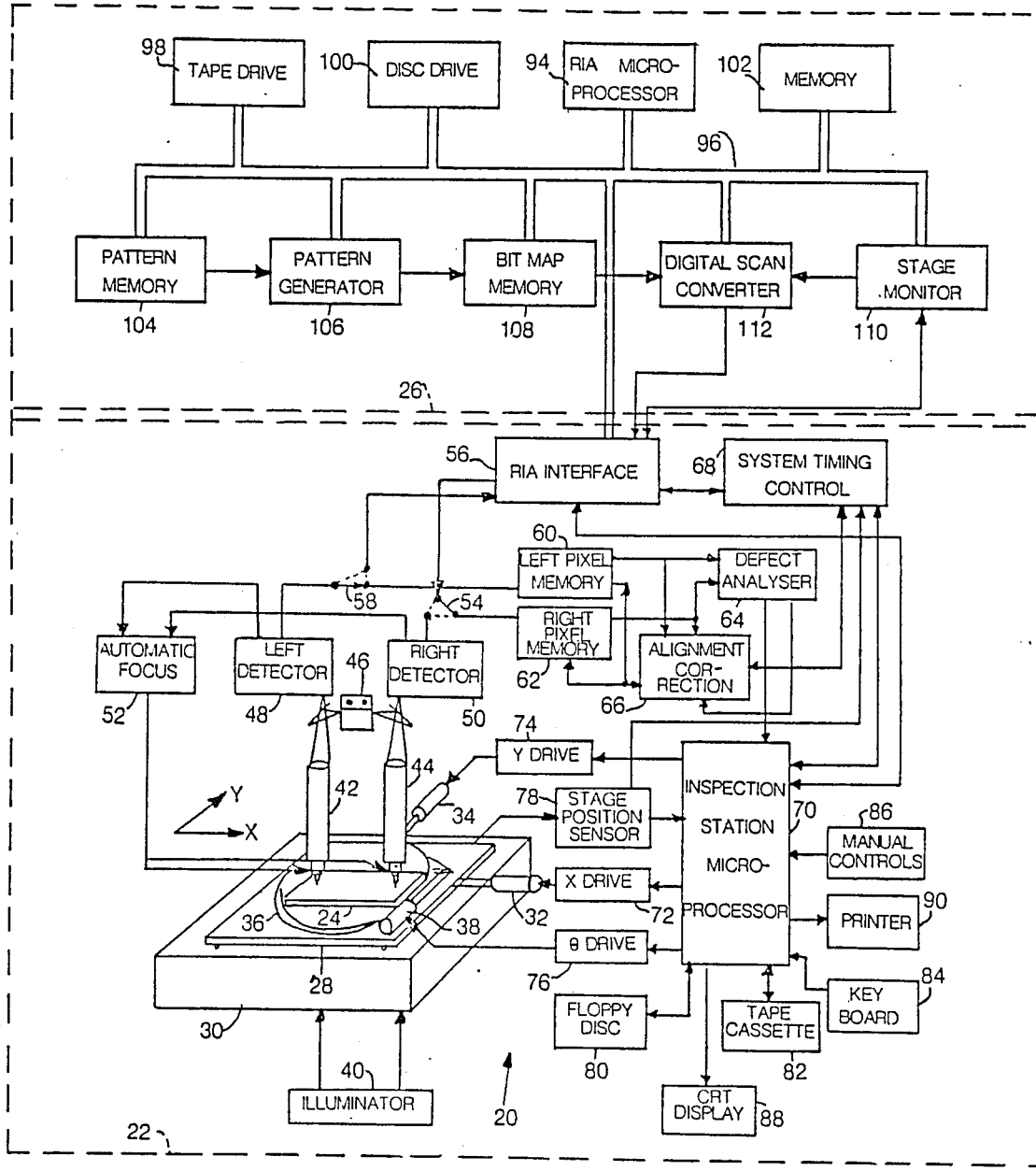
FIG. 1 is a functional block diagram of a reticle inspection system according to the present invention, including an inspection station portion and a reticle inspection adapter portion.

Referring now to FIG. 1 of the drawing, the preferred embodiment of a reticle inspection system according to the present invention is schematically illustrated at 20. The reticle inspection system 20 includes an inspection station 22 for inspecting a reticle or photomask 24 for defects, and a reticle inspection adapter 26 for generating a digital representation of the reticle from a stored database which is in a high-level description. The inspection station 22 includes an air-bearing stage 28 mounted on a granite table 30 for transporting and positioning the reticle or photomask 24 to be inspected. The stage 28 is movable in the X and Y directions by stepper motors and lead screws that are schematically illustrated at 32 and 34, respectively. A reticle holder 36 is rotatable in the $\theta$ direction by a motor at 38. A reticle to be inspected is mounted on the reticle holder which is rotated in the $\theta$ direction to align features of the reticle with the X and Y directions.

The inspection operation is performed on the reticle 24 by comparing two digital representations of a small area portion of the reticle. One digital representation of the reticle is formulated by optical means. The other digital representation is optionally formulated either by optical means or from a stored database. The optical means includes an illuminator 40, disposed beneath the granite table 30, which illuminates the bottom of reticle 24 through an opening in table 30. Also included are left and right inspection optics 42 and 44, respectively, which project images of the reticle onto a binocular view head 46, and onto left and right detectors 48 and 50, respectively. The binocular view permits viewing of a magnified image of the reticle by an operator. The inspection optics 42 and 44 are automatically focused by an automatic focus circuit 52, of a type corresponding to that disclosed in U.S. Pat. No. 4,247,203.

The reticle inspection system 20 can optionally inspect photomasks as well as reticles for defects. When inspecting a photomask, the left and right inspection optics are positioned so as to focus on identical portions of adjacent dice. Electronic representations of those adjacent dice are formed by the left and right detectors 48 and 50 and are later compared to find defects.

The position of a switch 54 determines whether an optical or a stored database representation is utilized for comparison to the optical representation from the left detector 48. If switch 54 is in the position shown in FIG. 1, the stored database representation of the reticle is transmitted to the inspection station 22 from the reticle inspection adapter 26 through an RIA interface 56. Another switch 58 optionally connects the output of the left detector 48 to the RIA interface 56 for calibration purposes, which will be explained in further detail below. Assuming that switch 58 is in the position indicated in FIG. 1, the output of the left detector is input into a left pixel memory 60. A right pixel memory 62 stores a corresponding representation of the reticle, either as measured by the right detector or as stored on a data base and constructed by the reticle inspection adapter, the selection of which depends upon the position of switch 54. Both the left and right pixel memories 60 and 62 are first-in-first-out (FIFO) type memory circuits that at any one time contain only a small fraction of the total optical and database representations. These memory circuits can be used to help cause a delay at their outputs between the left and right image under control of the Alignment Correct circuit 66.

Data stored in the left and right pixel memories 60 and 62 are compared to each other by a defect analyzer 64 to locate and characterize defects in the reticle 24. In order to electronically provide dynamic alignment of the two representations of the reticle, an alignment correction subsystem 66 is utilized which controls the relative delay between the left and right images. A system timing control 68 provides timing signals to synchronize the optical and database representations of the reticle, as well as to coordinate the sequences of the inspection process. Both the alignment correction subsystem and the system timing control will be described in further detail below. Timing signals and defect results are respectively input to an inspection station microprocessor 70 by the system timing control and the defect analyzer.

The inspection station microprocessor 70 controls the position and movement of the air-bearing stage 28 through X, Y and θ drives 72, 74, and 76, respectively, in response to program instruction and data received from a stage position sensor 78. Drives 72, 74, and 76 are preferably stepper motor controllers and sensor 78 is preferably comprised of optical encoders for the X and Y axis. Program instructions are prerecorded and input to microprocessor 70 via a floppy disk 80. System operation is controlled manually by the operator through a keyboard 84 and manual controls 86. Instructions to the operator or a visual display of the reticle may be displayed on a CRT display 88. Defect data resulting from the inspection operation is output on a printer 90, or stored by the tape cassette 82.

Figure 2:
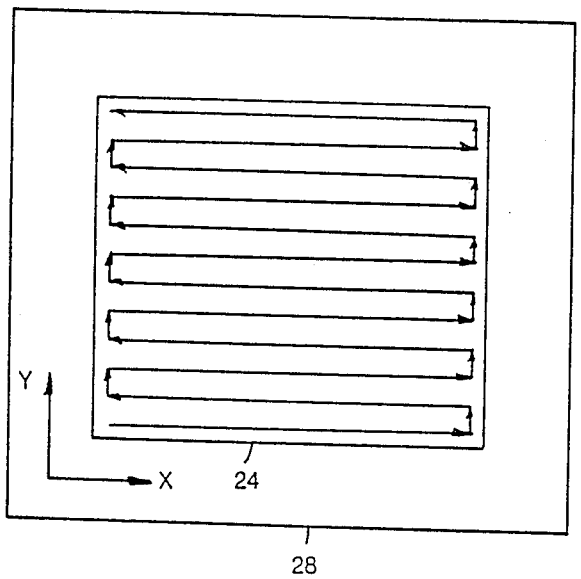
FIG. 2 is a diagrammatic representation of a sequence of stage movements in X and Y directions that are typically performed during an inspection operation by the present invention.

While the automatic focus circuit 52 maintains a focused image of the reticle 24 on the left detector 48, the inspection station microprocessor 70 directs the X and Y drives 72 and 74 to move the stage 28 in a serpentine path so that the entire portion of the reticle is sequentially viewed by the left detector. If a photomask is being inspected by comparing adjacent die, then the right detector 50 also views the inspected area. FIG. 2 shows the serpentine path described by the stage. The inspection operation occurs during the X translations, when the stage 28 is moving at a constant velocity. Between X translations, the stage is indexed in the Y direction to reposition it for the next X translation. As a matter of convenience, features on the reticle that are parallel to the X direction are hereinafter referred to as horizontal, and features parallel to the Y direction are hereinafter referred to as vertical.

The image sensing elements of detectors 48 and 50 are photosensors that are responsive to the intensity of light incident thereupon. Photosensors are dispersed at equally spaced positions along a line parallel to the Y direction. The extent of the reticle to which a photosensor responds is a function of the magnification of the inspection optics 42 and 44. The magnification results in each photosensor typically representing an area of $0.5 \times 0.5$ microns on the reticle although the system is capable of large sizes. Clearly smaller sizes or rectangular sizes could be used. At any one time, the photosensors view an area of the reticle that is one unit wide in the X direction and is N units long in the Y direction, where N equals the number of photosensors. By moving the stage 28 in the X direction at a constant velocity and by periodically scanning the electrical outputs of the photosensors, a representation of the reticle can be formed.

Figure 3:
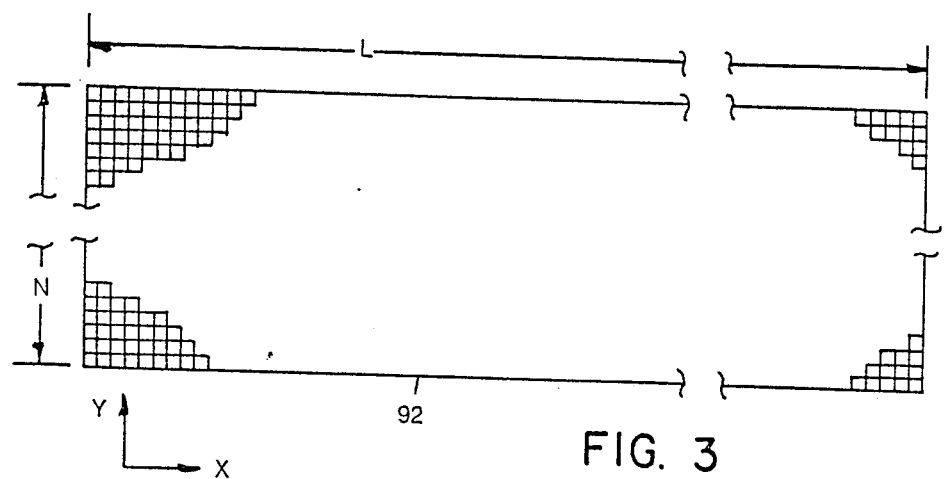
FIG. 3 is a diagrammatic representation of one swath of pixels formed as a result of a stage movement in the X direction.

FIG. 3 illustrates such a representation formed during an entire X translation of the stage. This representation is called a swath 92 and is composed of N pixels in the Y direction and L pixels in the X direction, where L is the number of scans performed on the photosensors during the X translation. Each scan of the N photosensors defines one vertical column of the swath. The output of each of the N photosensors is scanned L times, thus forming the $N \times L$ swath. A pixel is the rectangular element of which many compose the swath. Each pixel corresponds to a rectangular portion of the reticle. The Y dimension of each pixel is determined by the photosensor spacing and the optical magnification, while the X-dimension is determined by the stage velocity in X and the frequency of scanning the outputs of the photosensors. Each pixel has an X and Y address corresponding to the location of the portion of the reticle that is viewed by a photosensor. The pixel addresses are calculated from the position of the stage at the time that the photosensor output is measured. Each pixel has an associated value that corresponds to the intensity of light incident upon the photosensor. For the purposes of the present invention, it is sufficient to represent the pixel values as either white, grey, or black. A larger number of shades could, of course, be utilized.

The length L of the swath is determined by program instructions and extends to encompass the area to be inspected. There is an overlap between adjacent swaths to compensate for misaligning fattors such as warpage, positioning accuracy and thermal expansion. Since the pixel dimensions are preferably on the order of one-half micrometer, these misaligning factors require an overlap of tens of pixels.

Due to the enormous amount of memory that would be required to store a complete pixel map of the reticle 24, the comparison operation is continuously performed as the optical and database representations are formed. The speed of alignment between the optical and database representations as well as the speed of the defect detection determines the throughput of the reticle inspection system, and thus its productivity.

Now that a swath and pixel have been defined, let us return to FIG. 1 for an explanation of the function of the reticle inspection adapter 26. The purpose of the reticle inspection adapter is to construct pixels from a high-level stored database description and to supply those pixels to the inspection station 22 for comparison to those pixels generated by the left detector 48. The high-level database description used as input by the reticle inspection adapter is a conversion of the original database utilized to fabricate the reticle.

The fabrication database consists of a list of separate figures used as input to a pattern generating machine, such as an optical or E-beam pattern generating machine. The pattern generator machine sequentially exposes each figure onto the photomask or reticle being fabricated in order to create the pattern on the photomask or reticle as the superposition of many figures. A fabrication database typically consists of $1 \times 10^6$ figures. These figures are arranged in the fabrication database in a way that is convenient for the pattern generating machine. For inspection of the reticle, to facilitate the efficient construction of the bit map image and prevent excessive searching through the fabrication database, an off-line computer (not shown) converts the fabrication database into a swath wide format wherein each swath corresponds to a swath that will be taken by the left detector 48 of the inspection station 22 when the reticle or photomask is inspected.

Furthermore, each swath is divided into fractional swaths which are each equal in width to the swath's height. Each fractional swath in the converted database consists of all the figures needed to create the bit map for that fractional swath. Each fractional swath is sequentially placed in the converted database in accordance with the scanning path, as shown in FIG. 2. The converted database is then stored on magnetic tape and placed on the tape drive 98, whereby it is used directly or is transferred to the disc drive in preparation for the inspection.

The positions of the geometrical patterns in each fractional swath are specified by the coordinate locations and slopes of their edges. During the synchronized and simultaneous scanning of the reticle, the geometrical patterns of each fractional swath in the converted database are used to construct an image-like pixel representation, or bit map, of the reticle pattern by the reticle inspection adapter. As can be seen, only a small amount of the complete pixel representation appears in high speed memory at any one time. One advantage to this type of high speed construction, over that of storing a complete pixel representation, is that storage requirements are significantly reduced and become practical. In addition, the much slower disc drive 100 is fast enough to produce the geometrical representation of the database as it is required for inspection.

The reticle inspection adapter 26 performs its tasks of reconstructing the pixel representation and supplying a serial stream of pixels to the inspection station 22 under the control of an RIA microprocessor 94. All of the elements of the reticle inspection adapter are interconnected via a bus 96. A tape drive 98 and a disc drive 100 are provided for the storage of the converted high level database and RIA program instructions. A memory 102, retains the program instructions during operation, and a double-buffered pattern memory 104 retains portions of the high-level database, or fractional swath, as it is read from the tape or disk drive. The double-buffered pattern memory 104 serves as a buffer for a pattern generator 106 which converts the geometrical patterns of the high-level database into the black and white pixels of the pixel representation, and continuously stores the result in a double-buffered bit map memory 108.

To provide synchronization between the optical and database representations of the reticle 24, a stage monitor 110 in the reticle inspection station 22 monitors the output of the stage position sensor 78 through the system timing control 68. At the appropriate time, the stage monitor directs a digital scan convertor 112 to transfer from the bit map memory 108 to the RIA interface 56 a serial stream of pixel values corresponding to the database representation. The digital scan convertor also generates grey pixels at white-to-black and black-to-white transitions to simulate the edge transitions detected by the inspection station. This serial stream of pixel values (database representation) is stored in the right pixel memory for alignment and comparison to pixel values from the left detector 48 (optical representation).

Figure 4:
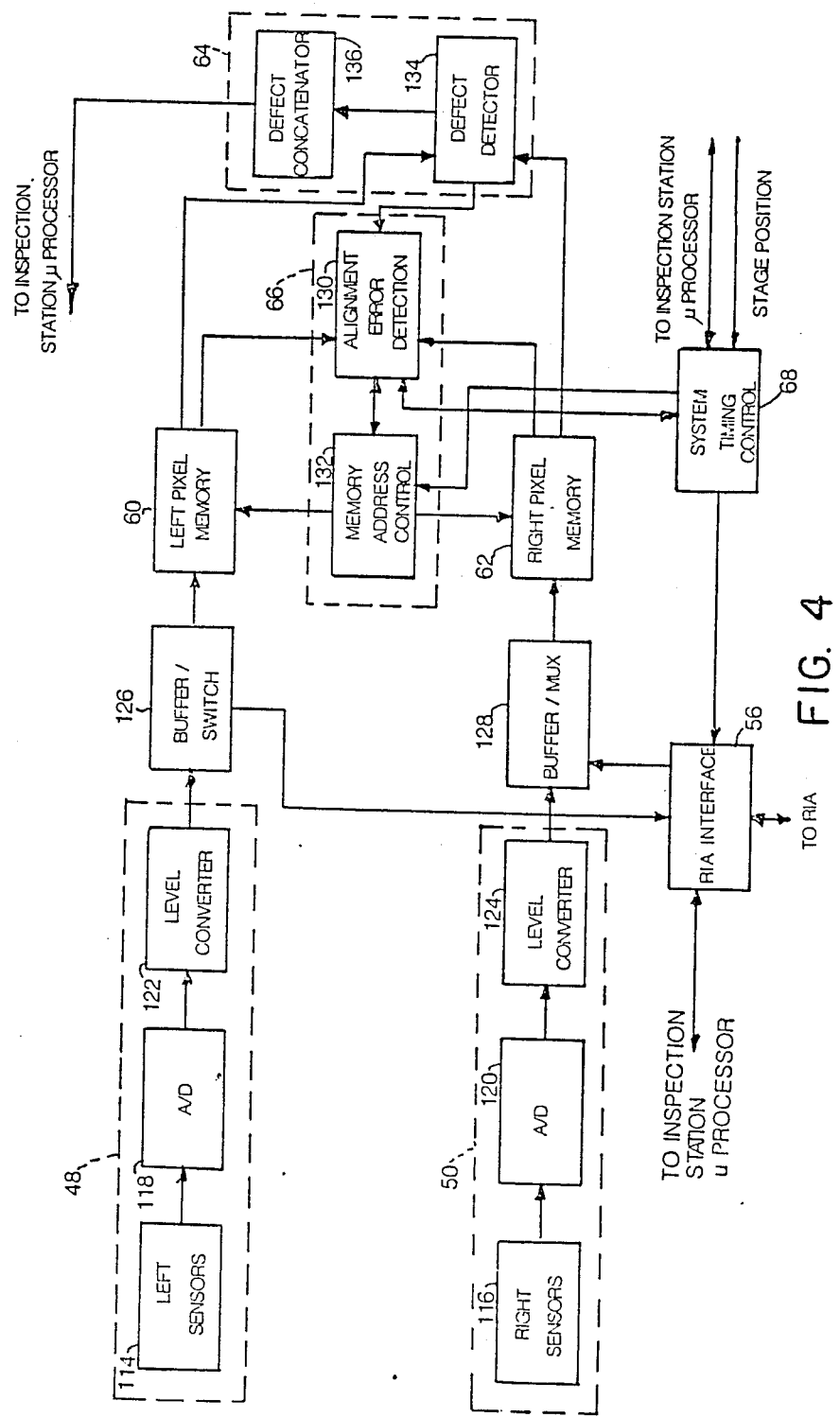
FIG. 4 is a functional block diagram of pixel generation and alignment correction circuits of the reticle inspection system of FIG. 1.

FIG. 4 illustrates the operation of the detection, alignment, and defect analysis portions of the inspection station 22. The left and right detectors 48 and 50 are each respectively composed of sensors 114 and 116 (the photosensors described above), analog to digital converters 118 and 120, and level converters 122 and 124. As the photosensors are scanned one at a time, the A/D converters and the level converters output a serial stream of pixel values representing white, grey, or black. The sensors generate proportional signals in response to the intensity of light incident thereupon. The signal length of the sensor signals is converted into one of sixteen digital values by the A/D converters and which is in turn converted into one of three values by the level converters. A buffer/switch 126 permits the output of the left detector to be directed to the reticle inspection adapter for calibration purposes. A buffer/multiplexer 128 selectively connects either the right detector or the RIA interface 56 to the right pixel memory 62, depending on whether a die-to-die comparison or a reticle to database comparison is desired.

Once the left and right pixel memories 60 and 61 have been filled with pixel data, the alignment and defect detection processes are initiated. As mentioned above, the pixel memories retain just a portion of the pixel representation of the reticle, and in the preferred embodiment, for example, they retain only the pixel values from the sixteen most recent scans. As each scan is completed, the oldest scan is shifted out of the memory to make room for the upcoming scan. Each pixel memory thus retains a matrix of size $N \times 16$, corresponding to pixels from the sixteen most recent scans. Both alignment and the defect detection are functions that are continuously performed as the pixel data passes through the pixel memories.

Alignment is accomplished between the pixel memories 60 and 62 by the alignment correction subsystem 66, which includes an alignment error detection circuit 130 and a memory address control circuit 132. Briefly, the alignment error detection circuit compares portions of the pixel memories and instructs the memory address control circuit to define those portions so as to minimize alignment error. This will be explained in greater detail below.

Defect detection is performed on these same portions of the pixel memories that the alignment circuitry uses. A defect detector 134 compares the aligned pixel memories and defines defects as differences between them. The operation of the defect detector is described in more detail in U.S. Pat. No. 4,247,203. A defect concatenator 136 is responsive to the output of the defect detector and acts to group the defects that are detected, since some defects are large enough to be detected several times. The results of the defect analysis are then made available to the inspection microprocessor 70 for recording.

The system timing control 68 provides several timing and control functions for the inspection station 22 and the reticle inspection adapter 26. One function is to control swath length by tracking the position of stage 28 with the aid of stage position sensor 78. Another function is to trigger the scanning of the sensors 114 (and 116 if used). Since the system timing control triggers the scanning of the sensors, it controls the pixel size in the X direction. The system timing control can compensate for slow moving alignment errors such as those resulting from stage velocity variations or low frequency stage vibrations by modulating the pixel size in the X direction, as will be described below. Still another function of the system timing control is to distribute a pixel clock signal that regulates the flow of pixel data through the alignment error detector 130 and the pixel memories 60 and 62. Synchronization between the optically measured pixels and the database pixels is provided by the system timing control through the RIA interface 56.

Figure 5:
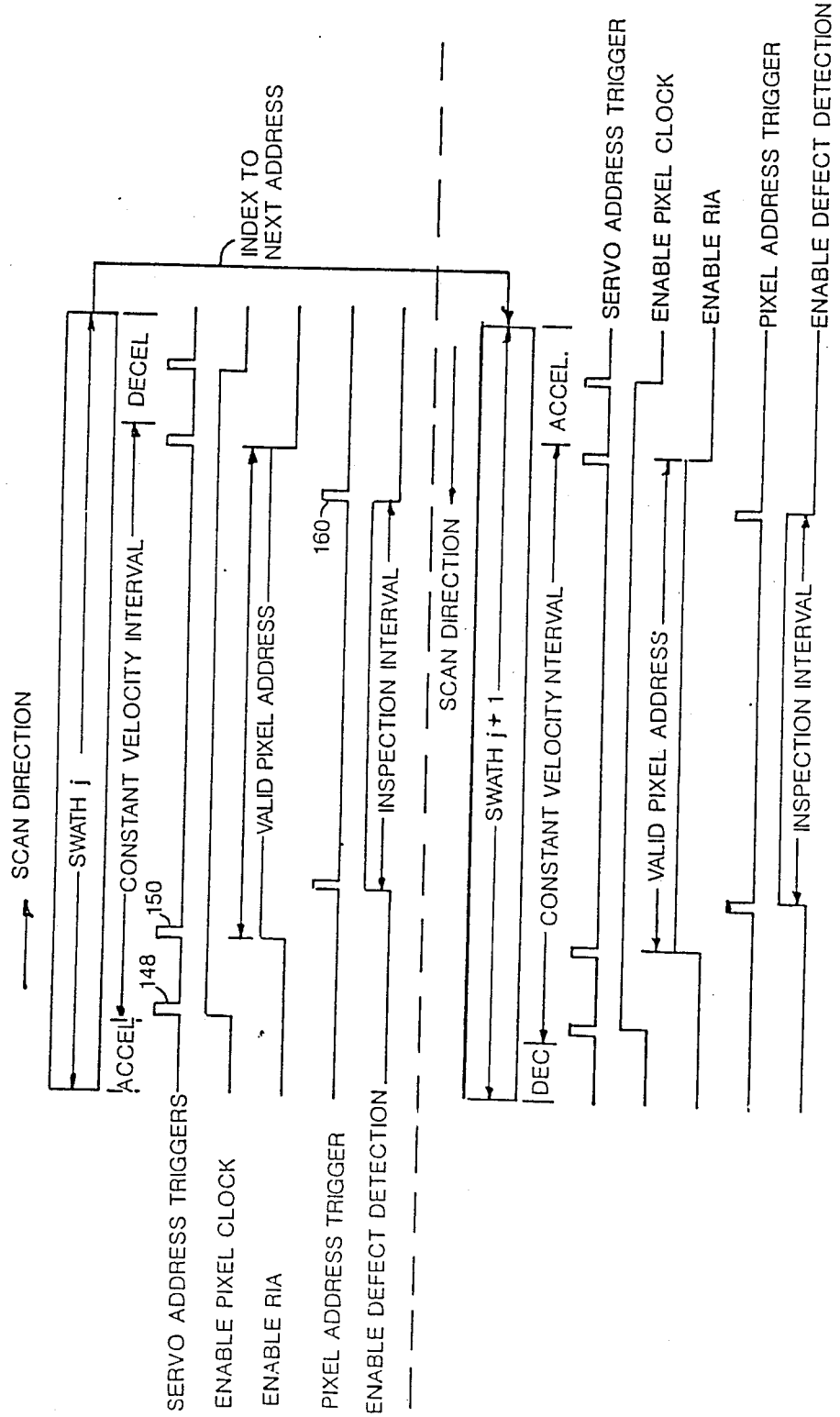
FIG. 5 is a timing diagram of the inspection station and illustrates the various operational modes during an inspection operation.
Figure 6:
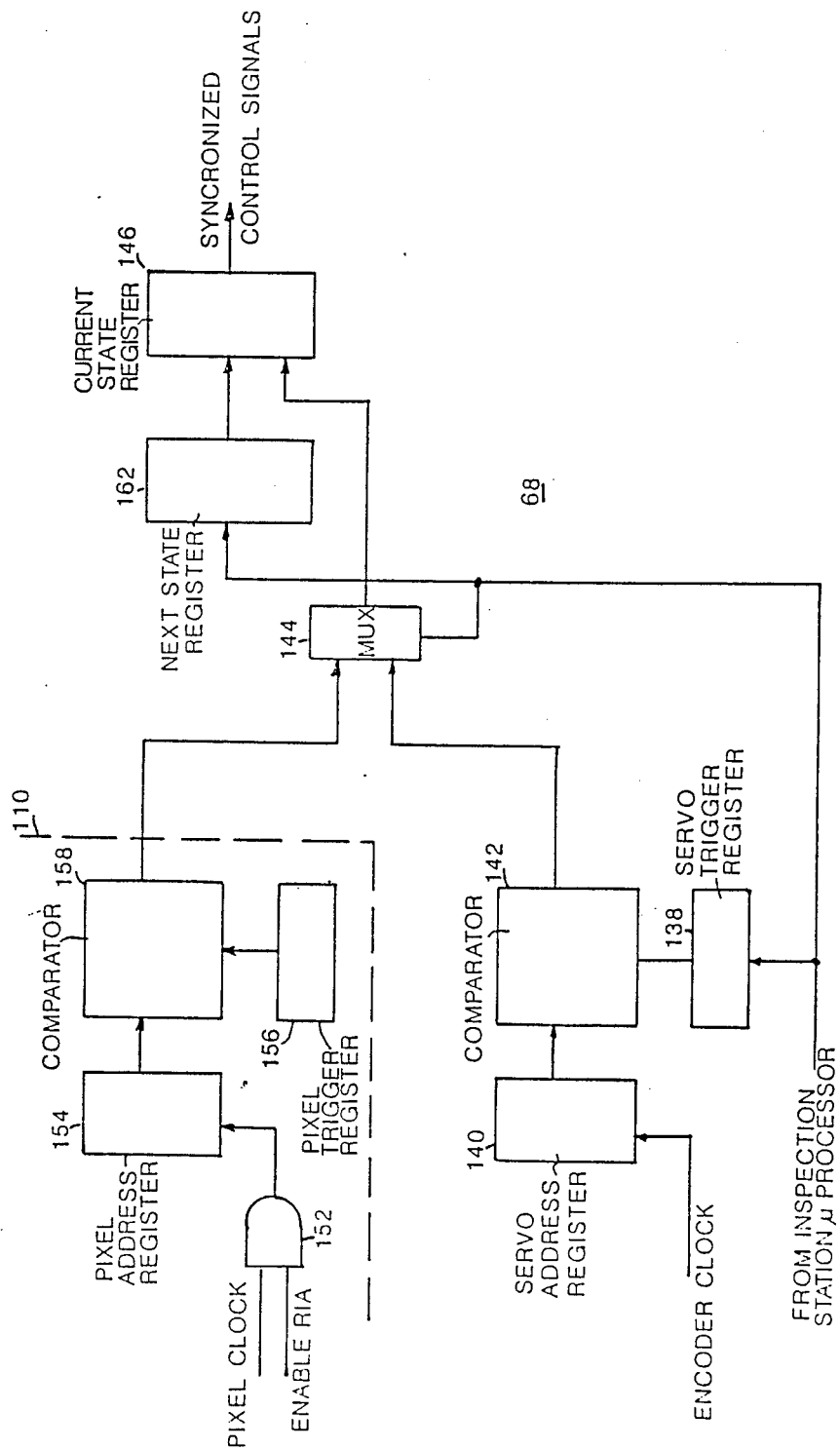
FIG. 6 is a functional block diagram of a scan synchronization circuit used in synchronizing measured and stored representations of a reticle or photomask during an inspection operation.

FIGS. 5 and 6 illustrate the method employed to synchronize the reticle inspection adapter 26 to the sub-inspection station 22. At the start of each swath, the stage 28 accelerates from rest, then proceeds at a constant velocity until it is near the end of the swath, whereupon it decelerates to a stop. After indexing in the Y direction by an appropriate amount, the next swath begins. In order to know when to start and stop the swaths and in order to mesh together adjacent swaths, the system timing control 68 monitors the position of the stage as indicated by the stage position sensor 78. To do so, microprocessor 70 loads a servo address into a servo trigger register 138. As the stage moves, an encoder clock signal from the stage position sensor 78 increments a servo address register 140, which thus indicates the servo address of the stage position. When a comparator 142 indicates that the stage has reached the prestored servo address, a signal is sent through a multiplexer 144 to a current state register 146 which outputs the appropriate control signals. Servo address triggers 148 and 150 (FIG. 5) are respectively used to enable the pixel clock and to enable the reticle inspection adapter (RIA) 26 to begin counting pixel addresses.

After the second servo address trigger 150 enables the reticle inspection adapter 26, and while the alignment correction subsystem 66 is aligning the pixel memories, the stage monitor 110 counts pixels to trigger a valid inspection interval. The pixel clock and enable RIA signals are combined by an AND gate 152 and increment a pixel address register 154 to count pixels. When the pixel count reaches a prestored value held in a pixel trigger register 156, a comparator 158 outputs a signal through the multiplexer 144 to the current state register 146. This initiates the inspection process, which continues until the next pixel address trigger 160 is reached. The RIA microprocessor 94 loads the pixel address triggers into the pixel trigger register according to its program instructions. The inspection station microprocessor 70 acts to load servo address triggers into the servo trigger register 138, as well as control the multiplexer to selectively connect the proper comparator to register 146. Microprocessor 70 also loads the next control instruction into a next state register 162, which serves as an instruction buffer so that register 146 can be updated quickly and without the delay that would result from an update directly from microprocessor 70.

Figures 7A, 7B:
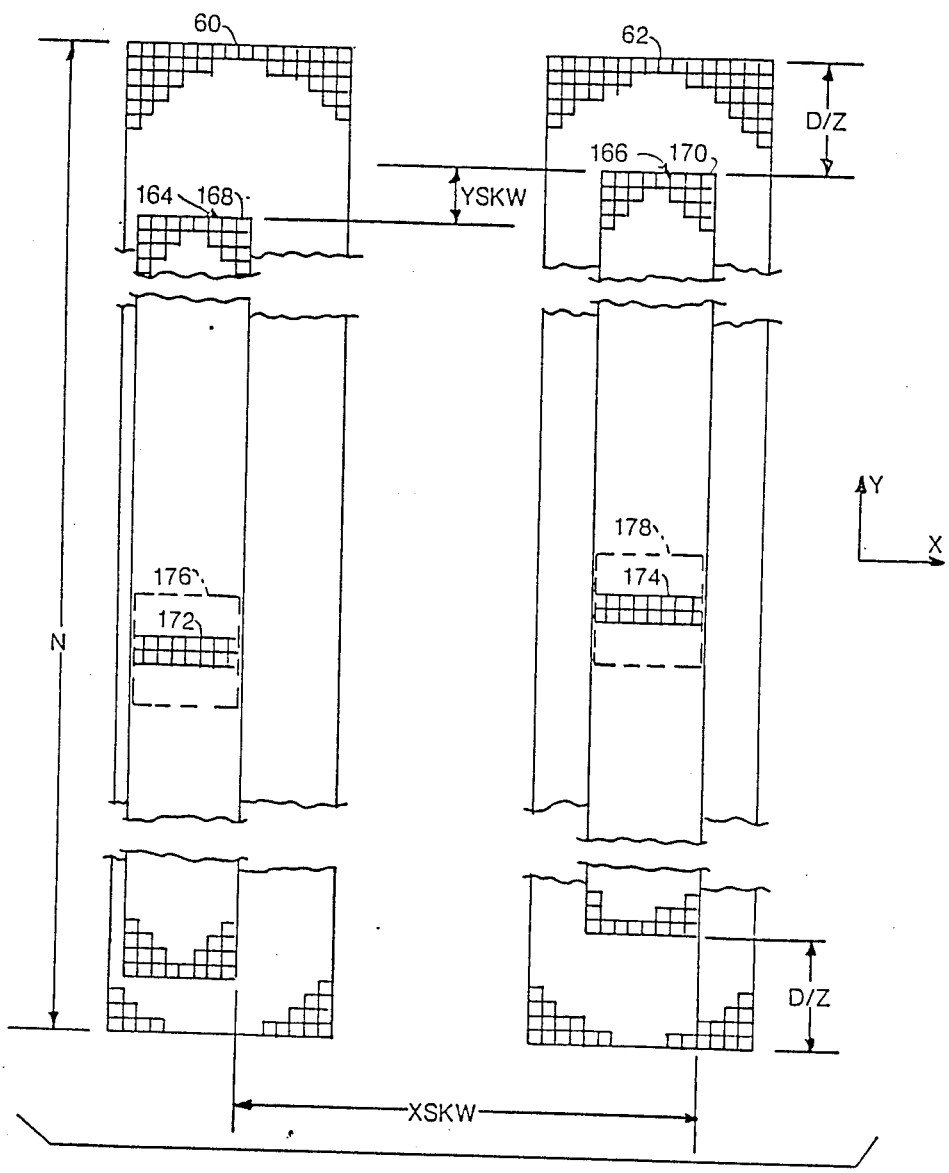
FIG. 7a is a diagrammatic representation of right and left pixel memories illustrating the relative positioning of inspection windows within the pixel memories.
FIG. 7b is a diagram that illustrates the labeling of pixels within an alignment detection matrix.

A diagrammatic representation of the left and right pixel memories 60 and 62 is illustrated in FIG. 7a. Each pixel memory contains sixteen columns of pixel values, each column having N rows, where N equals the number of photosensors. Both the alignment correction subsystem 66 and the defect analyzer 64 view only a portion of the pixel memories that is eight columns wide. Those portions of the pixel memories are labeled left and right inspection windows 164 and 166. The inspection windows are located within the pixel memories in reference to left and right window origin addresses 168 and 170, which define the upper right corner of the respective windows. The X-dimension of the inspection windows is eight pixels and the Y dimension is less than N by an amount equal to D.

The task of the alignment correction subsystem is to continuously adjust the position of the two inspection windows 164 and 166 within their respective pixel memories so that a pattern feature, such as an edge, which at some instant in time is located in the center of an inspection window, has its matching feature located within the 8 pixel bounds of the inspection window on the opposite side. Thus, the alignment correction subsystem insures that matching features in the left and right inspection windows always within $\pm 3$ pixels of each other. When the representations are so aligned, the defect analyzer can accurately detect defects by doing a comparison between windows, without being triggered by alignment or registration errors.

To align the two inspection windows 164 and 166, the alignment error detection circuit 130 gathers data during each pixel clock cycle by viewing the pixel values within left and right alignment matrices 172 and 174. The alignment matrices are two rows high and eight columns wide and are labeled according to FIG. 7b. At the beginning of a scan cycle, the alignment matrices are positioned at the top of their respective inspection windows. During each pulse of the pixel clock, the alignment circuit examines the pixel values of the alignment matrices and looks for horizontal and vertical features. Each pulse of the pixel clock advances the alignment matrices downward ($-Y$ direction) by one pixel. This process continues throughout the sensor scan until the alignment matrices are positioned at the bottom of the windows. At that point, a decision is made by the alignment circuit whether or not to make an alignment correction of $\pm 1$ pixel in either, or both directions. If an alignment correction is necessary, the memory address control circuit 132 adjusts the left and right window origin addresses 168 and 170 which effectively repositions the windows within the pixel memories. Before the start of the next scan, the oldest column of pixel data is shifted out of the pixel memories, and the newest column is shifted in. The next scan begins with the alignment matrices positioned at the top of the repositioned windows.

The offset of the left and right inspection windows 164 and 166 relative to each other, equals the value YSKW (Y skew) in the Y direction and the value XSKW (X-skew) in the X direction. YSKW equals the differences in the Y coordinates of the left and right window origin addresses 168 and 170, and XSKW equals the difference in the X coordinates. By fully advancing one window in X and fully retarding the other, the maximum alignment error that can be tolerated is equal to eight pixels. Similarly, in Y, the maximum alignment error that can be tolerated is equal to D.

Defect detection is performed by the defect detector 134 on the pixels within left and right defect detection matrices 176 and 178. These matrices are eight rows high and eight columns wide with the alignment matrices 172 and 174 at their centers. The defect detection matrices follow the alignment matrices as they advance downward through the inspection windows 164 and 166. If the alignment windows are properly aligned, the defect detection matrices will also be properly aligned.

Several of the advantages to this approach of alignment correction are that the alignment is a high-speed, continuous process, no stopping or restriction of the pixel stream is necessary, and continuous correction of alignment can be performed.

The described alignment correction system can be made very responsive since there is no mass which must be moved, such as might be the case if one tried to move a physical object such as the objective to effect alignment. Although the total registration errors present during a reticle inspection may often exceed the range allowed by the described alignment correction system, these errors tend to be slow moving and can easily be compensated. In particular, a slow moving Y-alignment error, which might be caused by reticle rotation, can be detected by monitoring the average value of YSKW during a swath. The misalignment can then be corrected at the end of the swath by varying the amount of indexing on the Y-direction before the next swath is started. Similarly, slow moving X alignment errors, beyond the range of the above described X-alignment correction system, such as those caused by stage velocity errors, stage vibration, or thermal effects, can be detected by monitoring the XSKW average value during a swath, and can be corrected by modulating the X-dimension of the optical pixels. Modulation has the effect of slightly advancing or retarding the optical representation so as to align it with the database representation. This method of extending the alignment range is described in more detail below.

Figure 8:
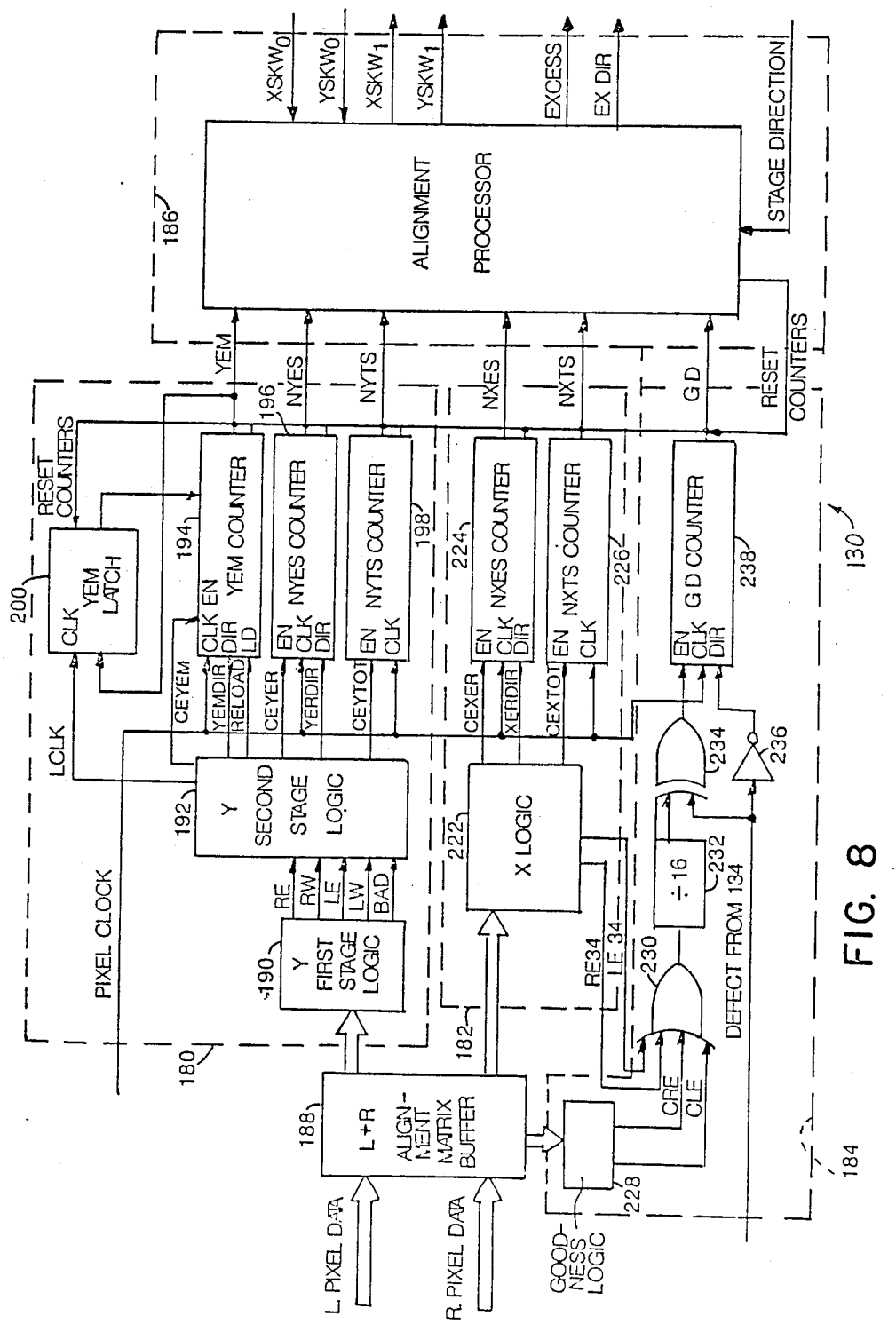
FIG. 8 is a functional block diagram of an alignment error detection circuit that dynamically detects alignment errors in both X and Y directions.

Alignment error detection is performed by the circuit illustrated in FIG. 8. This circuit operates upon the 2×8 left and right alignment matrices 172 and 174 (FIG. 7a) to quantify alignment errors. The circuit is composed of four basic sections: (1) a Y error detector 180 that measures alignment errors in the Y direction, (2) an X error detector 182 that measures alignment errors in the X direction, (3) a goodness detector 184 that measures the quality of alignment, and (4) an alignment processor 186 that accumulates the result of sections 1, 2, and 3 and decides whether alignment corrections are required. The Y error, X error, and goodness detectors all operate on the pixel values of the alignment matrices that are stored in an alignment matrix buffer 188, and which is updated each cycle of the pixel clock.

The Y-error detector 180 and the X-error detector 182 together are best described as a 2-dimensional phase detector, insomuch that this detector can readily determine even for large errors the absolute magnitude and direction of the average skew present at the end of each sensor scan. The novel method taught herein allows the instantaneous sensing of large misalignments, such as those caused by scanning reticles with large areas devoid of patterns, and which would not be sufficiently corrected by prior art systems. Alignment systems which depend on pattern information for operating their alignment system can behave improperly when there are large areas devoid of pattern. In this case no information is being sent to the alignment system, yet alignment errors continue to accumulate, so that the alignment may be several pixels removed from correct alignment when pattern is again encountered. If such a misalignment condition is not rapidly corrected, misalignment will be detected by the defect detectors and incorrectly reported as faults. An alignment system, such as that taught by Levy, will behave erratically when instantly encountering several pixels of misalignment and will therefore cause severe misalignment fault detections. Prior art alignment systems are not suitable for reticle inspection and can not be practically modified to perform such inspections properly.

Turning first to the Y error detector 180, its purpose is to identify horizontal features in the left and right images and to count the number of pixels that those horizontal features are offset from each other. To accomplish these tasks, the Y error detector has a first stage logic 190 to identify horizontal edges and color (B, G or W), a second stage logic 192 to determine valid measurement intervals and direction of error, and three counters 194, 196, and 198 and a latch 200 to count the measured errors. The first and second stage logic are implemented by programmable array logic (PAL) circuits.

To accomplish its functions of identifying horizontal edges and color, the first stage logic 190 examines the content of two pixels within each alignment matrix. Specifically, pixels in row 0 and columns 0 and 1 (hereinafter denoted as 0,0 and 0,1) are monitored at each pixel clock cycle. A valid horizontal edge is encountered when, for example, both pixels 0,0 and 0,1 are white at pixel clock $t_0$, both pixels are grey at $t_1$, and both pixels are black at $t_2$, where $t_0$, $t_1$, and $t_2$ are three consecutive pixel clock cycles. Valid horizontal edges are also encountered when pixels 0,0 and 0,1 are both white at $t_0$ and both black at $t_1$. These valid horizontal edges are respectively denoted W>G>B, and W>B. Valid horizontal edges are also encountered in the transitions B>G>W, and B>W.

When a valid edge is encountered in the right alignment matrix 174, (FIG. 7a) the first stage logic 190 outputs a positive pulse on an RE output line. When a B>G>W or a B>W transition is complete, an RW line is toggled logic high to indicate that the color of pixels 0,0 and 0,1 are now white. When a W>G>B or a W>B transition is complete, RW goes logic low to indicate that pixels 0,0 and 0,1 are now black. LE and LW are equivalent to RE and RW, but indicate edges or color of pixels 0,0 and 0,1 of the left alignment matrix 172. A signal denoted BAD is logic low when pixels 0,0 and 0,1 of the right alignment matrix agree in color and pixels 0,0 and 0,1 of the left alignment matrix also agree in color, although agreement in color between right and left is not required. If pixels 0,0 and 0,1 disagree in either the right or the left alignment matrix, BAD is logic high, thus indicating the presence of a diagonal edge. Although the diagonal edge is ignored for alignment purposes, it must first be detected by the system before it can be ignored.

Figure 9:
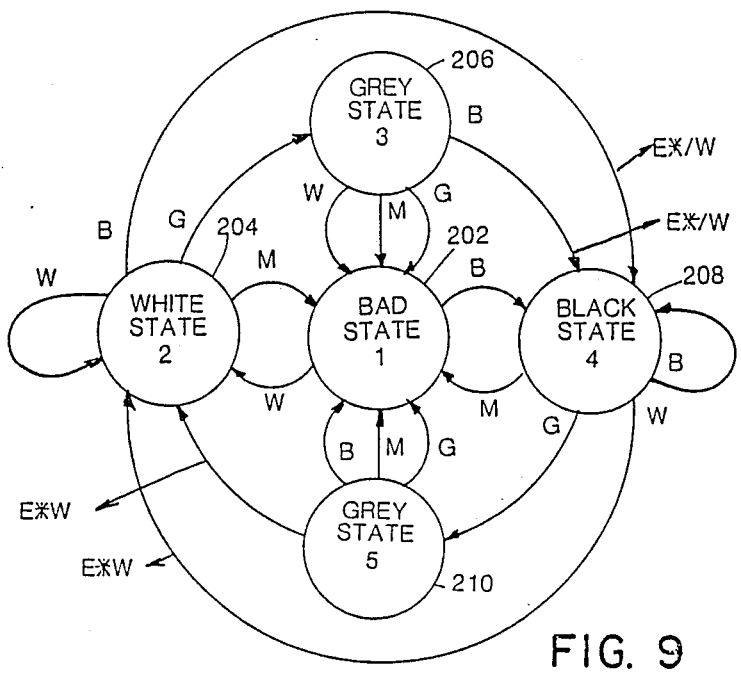
FIG. 9 is a logic diagram of a first stage of Y alignment detection-utilized by the alignment error detection circuit of FIG. 8.

FIG. 9 is a state diagram which illustrates the logic that is imbedded in the first stage logic PAL. This logic is duplicated for both left and right alignment matrices and independently determines the values for LE and LW and RE and RW. Five states are defined as follows: State 1 (202) occurs when pixel 0,0 is not the same color as pixel 0,1 (denoted as M) or when there is a G>G or a W>G>W or a B>G>B transition. When either the left or the right logic is in State 1, BAD is logic high. State 2 (204) occurs when pixels 0,0 and 0,1 are both white. State 3 (206) occurs when pixels 0,0 and 0,1 both make the transition W>G simultaneously. State 4 (208) occurs when pixels 0,0 and 0,1 both make either the transition W>B or the transition W>G>B. State 4 can be entered directly from state 2 or intermediately through state 3. Upon arrival at stage 4, an edge is indicated by pulsing RE or LE and the color is changed to black by toggling RW or LW to logic low. State 5 (210) occurs when pixels 0,0 and 0,1 both make the transition B>G simultaneously. State 2 can be entered from state 4 either directly by the transition B>W, or through state 5 by the transition B>G>W. When state 2 is entered from state 4 or state 5, RE or LE is pulsed, denoting a high valid horizontal edge, and RW or LW is toggled to logic high, denoting that the color is now white.

The function of the second stage logic 192 is to act on the data generated by the first state logic to identify valid alignment errors, and to output signals to the counters 194, 196, 198, and latch 200 to count the number of measurement intervals and the net alignment error in Y. A valid measurement interval begins when one alignment matrix indicates a horizontal edge and changes to a different color than the second alignment matrix. The valid measurement interval ends when the second alignment matrix indicates a horizontal edge and changes to the same color as the first matrix.

As an example, let us assume that initially both matrices are white, that is, they are both in state 2. If the left matrix encounters an edge, it shifts to black, state 4. If then three pixel clock cycles later, the right matrix encounters an edge and shifts to black, the measured alignment error is three pixels. Continuing with this example, let us further assume that ten pixel clock cycles later, the left matrix indicates an edge and shifts back to white. This begins another valid measurement interval which ends three pixel clock cycles later when the right matrix indicates an edge and shifts to white. Again the measured alignment error is three pixels. In this example, the black features that were sensed were thirteen pixels in length and the left one was offset three pixels from the right. The alignment error was measured twice and found to be three pixels each time. The direction of the error was thus found to be "left leading".

The Y second stage logic 192 increments the YEM (Y error measure) counter 194 during each pixel clock cycle of a valid measurement interval. The YEM counter counts up for each clock cycle in which the left matrix is leading and down for each clock cycle in which the right matrix is leading. The resultant count in the YEM counter is a net number of pixels as a measure of the Y alignment error. The Y second stage logic also increments the NYES (net number of Y error samples) counter 196 for each left leading valid measurement interval and decrements the counter for each right leading interval. The resultant count in the NYES counter is the net number of measurement intervals. The NYTS (number of Y total samples) counter 198 is incremented for each valid measurement interval, regardless of error direction and indicates the total number of valid error intervals. The NYTS counter is also incremented when coincident edges are encountered. These numbers are used by the alignment processor 186 to determine when a Y alignment correction is required and the magnitude of the correction.

Figure 10:
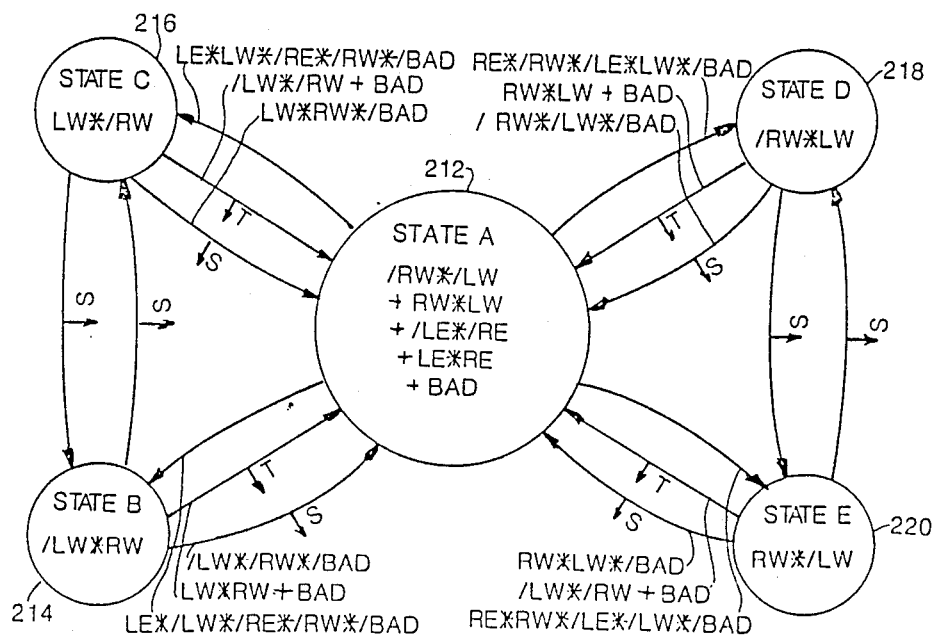
FIG. 10 is a logic diagram of a second stage of Y alignment detection utilized by the alignment error detection circuit of FIG. 8.

FIG. 10 is a state diagram which illustrates the logic that is imbedded in the PAL's that define the second stage logic 192. The nomenclature of FIG. 10 is as follows: RE=LE=RW=LW=BAD= logic high; /RE=/LE=/RW=/LW=/BAD=logic low; * means logic AND; + means logic OR. Again, five states are defined. State A 212 is a rest state, that is to say that there exists no valid measurement interval either because both matrices are the same color, or because the BAD signal is high, indicating a non-horizontal edge. State A may occur, for example, when pixels 0,0 and 0,1 of the left alignment matrix are both white or black and pixels 0,0 and 0,1 of the right alignment matrix are both white or black, denoted as RW*LW, or /RW*/LW. If two horizontal edges are simultaneously indicated by the two matrices, denoted LE*RE, the state remains at state A, since this occurs when both representations are aligned.

The remaining four states occur during valid measurement intervals. The transition from state A (212) to state B (124) occurs when both matrices are white and the left matrix indicates a horizontal edge and a change to black. This transition is stated logically by the following: LE*/LW*/RE*RW*/BAD, which means that an edge is indicated by pixels 0,0 and 0,1 of the left matrix (LE) and pixels 0,0 and 0,1 of the left matrix are now black (/LW) and pixels 0,0 and 0,1 of the right matrix do not indicate an edge (/RE) and pixels 0,0 and 0,1 of the right matrix are both white (RW) and the BAD signal is logic low (/BAD). While in state B, the YEM counter 194 counts up one for each pixel clock. The direction of this error measurement is left leading, since the edge was indicated by the left matrix.

As defined above, a valid measurement interval ends when the second matrix (right in this example) indicates an edge and changes color to that of the first matrix (black in this example). In FIG. 10, this is shown as /LW*/RW*/BAD, meaning pixels 0,0 and 0,1 of the left matrix are black (/LW) and pixels 0,0 and 0,1 of the right matrix are black (/RW) and the BAD signal is logic low (/BAD). When this occurs, the measurements are to be saved since they are valid. An S in FIG. 10 thus indicates a save command. However, if while in state B, a second left edge is encountered changing pixel 0,0 and 0,1 of the left matrix to white, then a valid measurement did not occur. Alternately, if while in state B either the left or the right matrix indicates a BAD signal, then a valid measurement did not occur. In either of these cases, LW * RW +BAD, the state transfers back to state A and the measurement just made is thrown away. FIG. 10 indicates such a transition with a T.

The other three states operate in a similar fashion. If in state A, both left and right alignment matrices are black (/RW*LW) and then the left matrix indicates an edge (LE) which changes the left color to white (LW), then the logic transfers to state C (216). While in state C, the YEM counter counts up since this is a left leading measurement interval. If the right matrix indicates a shift (RW), then the measurement interval is valid and the state transfers to state A and that interval is saved. If, however, the left matrix indicates a shift back to black (/LW) or the BAD signal goes logic high, then the state transfers to A and the interval is discarded.

When the Y second stage logic 192 is in state B (214) or state C (216), a valid measurement interval can end without a transfer back to state A. This occurs when both the left and the right alignment matrices indicate an edge simultaneously, causing a transition from state B to state C or from state C to state B. If, for example, the logic is at state B, then left is black (/LW) and right is white (RW). If left shifts to white (LW) and right shifts to black (/RW) at the same pixel clock pulse, then the state transfers to state C and the measurement interval of state B is saved. When the right matrix then shifts to white (RW), the logic transfers to state A and a second measurement interval is saved. In this situation, both measurement intervals are valid.

The remaining two states, state D (218) and state E (220) operate in the same fashion as states B (214) and C (216), except that the sense of the alignment error is reversed. State D is reached from state A (212) by right shifting to black with left remaining white. A valid measurement interval occurs from State—D when left shifts to black. State E is reached from state A by right shifting to white and left remaining black. A valid measurement interval occurs from State E when left shifts to white. As above, a state D to state E or a state E to state D transition can occur with coincident edges in left and right. The YEM counter counts down for each pixel clock cycle in states D or E, since the error indicated by these two states is right leading. The NYES counter also counts down for each valid measurement interval involving states D or E.

Figure 11:
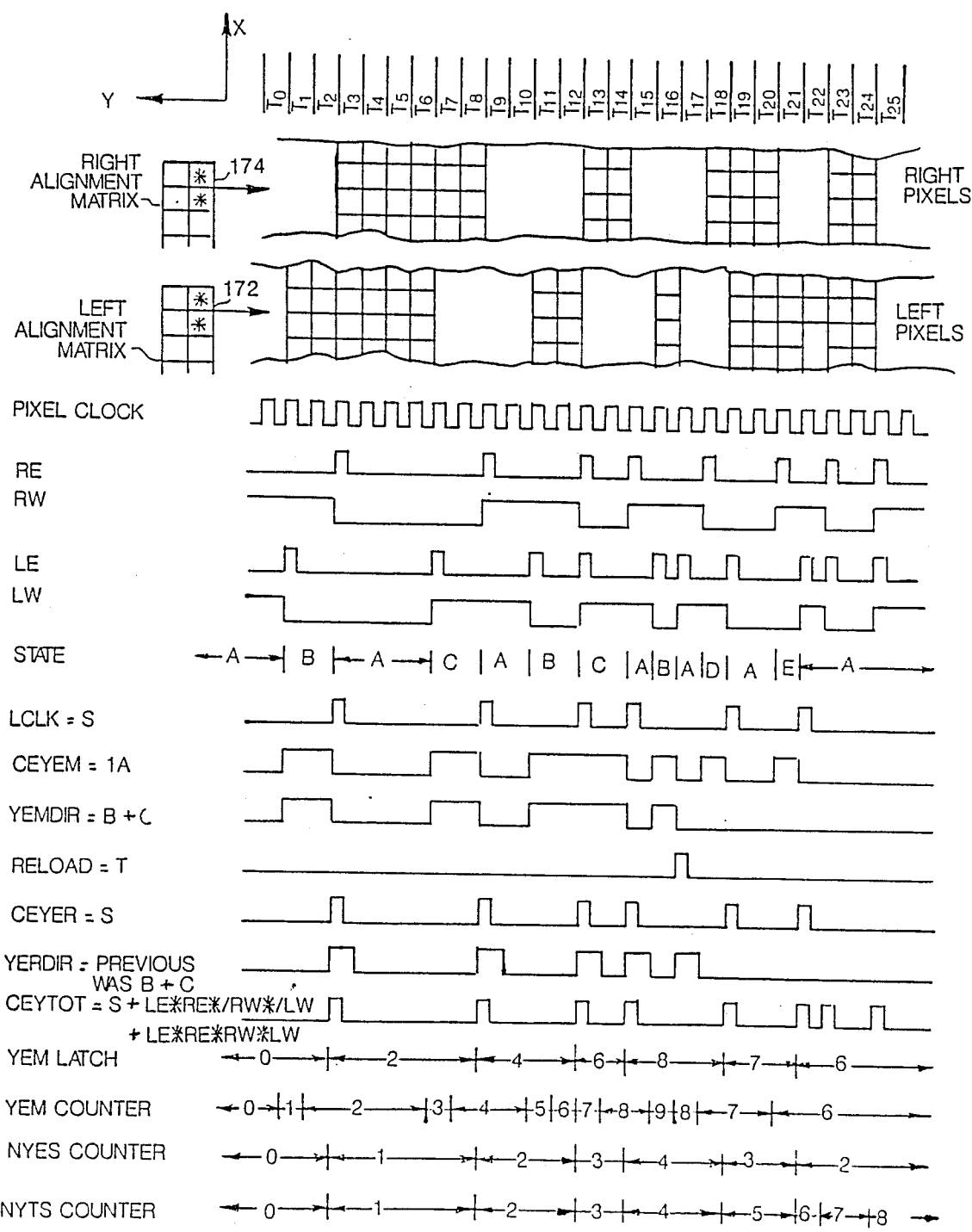
FIG. 11 is a timing diagram depicting the Y alignment detection function of the alignment error detection circuit of FIG. 8.

FIG. 11 is a timing diagram that illustrates the operation of the Y second stage logic 192 and the Y counters 194, 196, 198, and latch 200. A small portion of the left and right pixel memories 60 and 62 are shown, with the X-Y coordinate system rotated by one quarter revolution in a counterclockwise direction. Both the left and right alignment matrices 172 and 174 travel to the right (−Y direction) as time progresses from time $t_0$ to time $t_{25}$. The output signals of the Y second stage logic are defined in FIG. 11. In FIG. 11, LCLK pulses for each valid measurement interval. CEYEM indicates a state, other than state E, and thus is logic high if in state B, C, D, or E. YEMDIR indicates the direction of the Y alignment error and is logic high if in state B or C where the error is left leading. RELOAD is pulsed by a T transition marking the end of an invalid measurement interval. CEYER pulses for each valid measurement interval. YERDIR is logic high if the previous state was state B or C. CEYTOT pulses for each valid measurement interval and also for each coincident edge.

The above described outputs of the Y second stage logic 192 operate counters 194, 196, 198, and latch 200. The YEM counter 194 is enabled by CEYEM, and is clocked by the pixel clock according to the direction indicated by YEMDIR. If an invalid measurement interval is encountered, RELOAD reloads the last valid reading stored in the YEM latch 200. The output of the YEM counter, YEM, is input into the YEM latch, which is updated after each valid measurement interval by LCLK. The NYES counter 196 is enabled by CEYER for each valid measurement interval and counts in the direction indicated by YERDIR, which is up for left leading errors and down for right leading errors. The NYTS counter 198 is enabled by CEYTOT and clocked by the pixel clock to count the total number of valid measurement intervals plus coincident edges.

The following describes the timing diagram of FIG. 11:

$t_0$ both left and right matrices indicate white
$t_1$ left matrix encounters horizontal edge, shifts black
   LE pulses, LW toggles to logic low
   state B: left leading error
   YEM counts up one
$t_2$ still in state B, YEM counts up one
$t_3$ right matrix encounters horizontal edge, shifts black
   RE pulses, RW toggles to logic low
   state A: wait state
   LCLK pulses to indicate a valid measurement interval
   YEM latch loads YEM value
   NYES and NYTS counters count up one
$t_4$ still in state A
$t_5$ still in state A
$t_6$ still in state A
$t_7$ left matrix encounters edge, shifts to white
   LE pulses, LW goes high
   state C: left leading error
   YEM counts up one
$t_8$ still in state C, YEM counts up one
$t_9$ right matrix encounters edge, shifts to white
   RE pulses, RW goes high
   state A
   LCLK pulses to indicate a valid measurement interval
   YEM latch loads YEM value
   NYES & NYTS counters count up one
$t_{10}$ still in state A
$t_{11}$ left matrix encounters edge, shifts to black
   LE pulses, LW goes low
   state B: left leading error
   YEM counts up one
$t_{12}$ still in state B, YEM counts up one
$t_{13}$ left matrix encounters edge, shifts to white
   right matrix encounters edge, shifts to black
   LE pulses, LW goes high
   RE pulses, RW goes low
   coincident edge, shifts to state C: left leading error
   LCLK pulses to indicate a valid measurement interval
   YEM latch loads YEM value
   YEM counts up one
   NYES & NYTS counters count up one
$t_{14}$ still in state C, YEM counts up one
$t_{15}$ right matrix encounters edge, shifts to white
   RE pulses, RW goes high
   state A
   LCLK pulses to indicate a valid measurement interval
   YEM latch loads YEM value
   NYES and NYTS counters count up one
$t_{16}$ left matrix encounters edge, shifts to black
   LE pulses, LW goes low
   state B: left leading error
   YEM counts up one
$t_{17}$ left matrix encounters edge, shifts to white
   state A
   LCLK does not pulse: invalid measurement interval
   RELOAD pulses, YEM latch reloads YEM counter
$t_{18}$ right matrix encounters edge, shifts to black
   RE pulses, RW goes low
   state D: right leading error
   YEM count down one
$t_{19}$ left matrix encounters edge, shifts to black
   LE pulses, LW goes low
   state A
   LCLK pulses to indicate valid measurement interval
   YEM latch loads YEM value
   NYES counter counts down one
   NYTS counter counts up one
$t_{20}$ still in state A
$t_{21}$ right matrix encounters edge, shifts to white
   RE pulses, RW goes high
   state E: right leading error
   YEM counter counts down one
$t_{22}$ left matrix encounters edge, shifts to white
   LE pulses, LW goes high
   state A
   LCLK pulses to indicate valid measurement interval
   YEM latch loads YEM value
   NYES counter counts down one
   NYTS counter counts up one
$t_{23}$ left matrix encounters edge, shifts to black
   right matrix encounters edge, shifts to black
   LE pulses, LW goes low
   RE pulses, RW goes low
   still in state A
   NYTS counter counts up one
$t_{24}$ still in state A
$t_{25}$ left matrix encounters edge, shifts to white
   right matrix encounters edge, shifts to white LE pulses, LW goes high
RE pulses, RW goes high
still in state A
NYTS counter counts up one.

Returning now to FIG. 8, the operation of the X error detector 182 will now be explained. The purpose of the X error detector is to identify vertical features within the left and right inspection windows 164 and 166 (FIG. 7a) and to determine the sense of any X-direction alignment errors. Its task is somewhat easier than that of the Y error detector 180 because only the sense of the alignment error is required, not the magnitude. Alignment errors in the X-direction can only be corrected by one pixel for each sensor scan, otherwise the image in the pixel memories is torn. Therefore, it is critical that the sense of the error be correctly determined in the presence of several pixels of misalignment. It should also be noted that the X-alignment error detector described by Levy produces no error signal when the alignment is out by more than ±1 pixel, which again makes this method inappropriate for reticle inspection. To accomplish the above task and avoid the inadequacies of the prior art, the X error detector has an X logic circuit 222 to identify vertical edges, and two counters 224 and 226 to accumulate counts of the measured errors.

The X logic circuit 222 utilizes as input the 2×8 left and right alignment matrices stored in buffer 188. Unlike the Y logic circuits, the X logic circuit uses fourteen pixels in rows 0 and 1 and columns 1 through 7. The test for a vertical edge is quite simple: a vertical edge is indicated between columns 1 and 2 if pixels 0,1 and 1,1 are both black or both grey and pixels 0,2 and 1,2 are both white, or pixels 0,1 and 1,1 are both white or both grey and pixels 0,2 and 1,2 are both black. Similar logic tests are established to indicate the presence of a vertical edge between pixels 2 and 3, 3 and 4, 4 and 5, 5 and 6, and 6 and 7. All of the logic necessary to implement these tests are contained in the PAL's which comprise the X logic circuit 222.

The resultant output of this logic circuitry directs counters 224 and 226 to count the X alignment errors in much the same way as do the Y counters 196 and 198. The NXES (net number of x error samples) counter 224 is enabled by CEXER, which is output by the X logic 222. CEXER pulses high for each valid X error measurement which occurs whenever one alignment matrix has a valid edge and neither matrix has a diagonal, or whenever both matrices have valid edges not matched in position and neither matrix has a diagonal. The counting direction of the NXES counter is determined by XERDIR, which is positive for left leading X alignment errors and is negative for right leading X alignment errors. The NXTS (number of X error samples) counter 226 is enabled by CEXTOT, which pulses high whenever at least one alignment matrix has a valid edge and neither matrix has a diagonal edge.

The operation of the X logic 222 is illustrated in FIGS. 12 and 13. FIG. 12 shows a vertical feature 233 that is five pixels wide in the X direction and that is positioned within the right pixel memory 62 by three pixels in advance of its corresponding feature 223's position in the left pixel memory 60. Also shown are the relative positions of the alignment matrixes 172 and 174 during five different scans. Note that during any one scan, an alignment error in X will be detected several times; once at each pulse of the pixel clock. This occurs because the alignment matrices shift in the vertical direction at each clock pulse and recompute any detectable error. Since X alignment errors are measured from vertical edges, the same edge and the same error will be encountered at each clock cycle throughout the vertical extent of the edge.

During scan $s_0$, neither the left nor the right alignment matrix encounters a vertical edge between columns 1 and 7, and therefore the alignment error is not sensed. During scan $s_3$, the right alignment matrix has a valid edge between columns 3 and 4, while the left alignment matrix still has not seen the edge. To determine the sense of the X alignment error, the X logic 222 follows the truth table shown in FIG. 13. Two tests are performed: First, do the column 1 pixels of the left matrix agree with the column 1 pixels of the right matrix? Second, which matrix has an edge within the matrix that is closer to column 1? At scan $s_3$, the column 1 pixels disagree since the right column 1 pixels are black and the left column 1 pixels are white. As for the second test, only the right matrix has an edge inside, therefore the right matrix has an edge closer to column 1. The answer to the first test was disagree and the answer to the second test was right. According to the truth table, right is leading.

During scan $s_5$, both matrices have an edge inside. In applying the two tests, the column 1 pixels agree and the left matrix has an edge closer to column 1. Thus at scan $s_5$ the sense of the error is still right leading. Similar analyses at scans $s_6$ and $s_9$ will yield the same result: the right pixels are leading the left pixels. FIG. 12 was drawn assuming that no alignment corrections were made between scans, so as to demonstrate the logic of error sense determination. In actual practice, however, the inspection windows 164 and 166 (FIG. 7a) would be shifted between scans by one pixel in the X-direction, thereby repositioning the alignment matrices and reducing alignment errors.

Returning once more to FIG. 8, the function of the goodness detector 184 will now be described. The purpose of the goodness detector is to provide an indication of the quality of alignment information, since real defects in the inspection window can produce erroneous alignment information. To provide such information, the goodness detector sums the number of vertical and horizontal edges detected in pixels 0,3, 0,4, 1,3 and 1,4 of the left and right alignment matrices, divides by sixteen and compares the result to the number of defects detected by the defect detector 134 (FIG. 4). If the defects are the lessor of the two, then the alignment information is considered to be acceptable. Note that if the inspection windows were to become seriously misaligned through a major mask problem or system problem, the number of defects would then rise significantly in response to the misalignment and would exceed the comparison value.

The circuitry, necessary to accomplish this goodness test, includes a goodness logic PAL 228 which operates as does the Y first stage logic 190, except that the goodness logic PAL recognizes horizontal edges as columns 3 and 4 and generates corresponding signals CRE and CLE whenever edges are sensed in the right or left alignment matrices. The X logic 222 supplies signals RE34 and LE34 which are pulsed whenever a vertical edge is sensed between columns 3 and 4 in either the right or the left matrix. CRE, CLE, RE34, and LE34 are combined by an OR gate 230 and then divided by a divider 232. The resulting quotient and a DEFECT signal from the defect detector 134 (FIG. 4) are combined by an EXCLUSIVE-OR gate 234. The DEFECT signal is inverted by an inverter 236 then is input to the direction port of a GD counter 238. The GD counter is enabled by the output of gate 234 and is clocked by the pixel clock. Effectively, the GD counter counts up once for each sixteen vertical and horizontal edges sensed by the alignment matrices, and counts down once for each defect detected. Thus a positive number in the GD counter indicates good alignment information.

By using the values stored in the X and Y counters 224, 226, 194, and 198, the alignment processor determines whether an alignment correction is required, and, if so, in which direction. The decision to correct the alignment is based on the relative magnitudes of net error and total samples. Net error equals the number of left leading edges minus the number of right leading edges. These values are calculated by the NYES counter 196 and the NXES counter 224. Total samples equals the number of left leading edges plus the number of right leading edges plus the number of coincident edges. These values are calculated by the NYTS counter 198 and the NXTS counter 226. If the absolute value of the net error exceeds one-half of the total samples, then at least seventy-five percent of the errors were either left leading or right leading. At that point, the alignment error is significant enough to require correction, which is made in a direction as determined by the sense of the net error.

FIG. 14 represents this decision making process in a graphical fashion. Two variables are defined as functions of the net error and the total samples. A variable named "positive exceed" (PE) equals the net error (E) plus the absolute value of the net error minus the total samples (T). Another variable named "negative exceed" (NE) equals the negative of the net error plus the absolute value of the net error minus the total samples. PE and NE are normalized to T and plotted verses E normalized to T in FIG. 14. PE ranges from a value of $-T$ for E less than or equal to 0, up to $+T$ for E equal to T. Since the alignment error is significant enough to require correction when E equals or exceeds T/2, and since PE=0 at E=T/2, an alignment correction in the direction is required when PE is greater than or equal to 0. Similarly NE ranges from a value of $-T$ for E greater than or equal to 0, up to $+T$ for E equal to $-T$. An alignment correction in the $-$direction is therefore required when NE is greater than or equal to 0.

Even if the two pixel memories are exactly aligned, defects will be detected as alignment errors. Statistically, defect caused errors will be centered at zero net error, but will occasionally deviate from zero. By defining the point of error significance to be where PE or NE exceed zero, a no-correction band is created around zero net errors. This permits significant alignment errors to be corrected, but eliminates hunting for zero error and responding to defects as alignment errors.

The actual operation of the alignment processor 186 is somewhat more complex than just indicated. First, alignment corrections are required in both X and Y, so both PE and NE are calculated for both X and Y. Second, there is a hierarchy of alignment corrections; Y corrections are made before X corrections. The reason for this is that the total Y error can be measured during one scan, due to the direction of movement of the alignment matrices through the inspection windows, while the X error can be measured only one pixel at a time. Third the alignment processor uses weighted averages of net errors and total samples from a large number of previous scans so as to adapt the responsiveness of the alignment correction, in accordance with the pattern density and the quality of the recent patterns.

This adaptive alignment technique, using weighted averages, acts to slow the responsiveness to alignment correction when alignment of the patterns has been acceptable over a large number of recent scans and the pattern density has been reasonable. In contrast, the weighted averages act to increase responsiveness when recent alignment errors have been significant, or when the pattern density is low. This allows the alignment subsystem to be properly responsive to the varying pattern conditions encountered in reticle inspection. It should be noted that the alignment subsystem taught in Levy, is not adaptive and becomes sluggish when the pattern density is low, which in turn leads to poor alignment quality and misalignment faults being detected as actual defects.

Five values are stored by the alignment processor 186 for use in determining the significance of alignment errors. The positive excess function is calculated for both X and Y, and is stored in accumulators XPI and YPE (not shown). The negative excessor function is also calculated for X and Y, and is stored in accumulators XNE and YNE (not shown). An accumulation of the goodness parameter is stored in GOOD (not shown). Each of the five accumulators is decayed by an exponential decay factor of (1-1/2048) at each update so as to limit the impact of any one measurement. At the end of each scan, the X and Y counters are read and update values to the accumulators are calculated. If by adding an update value to an accumulated value, the sum exceeds zero, then an alignment correction is performed. If a correction is required in Y, the magnitude of the correction is YEM/NYTS. Due to the time required to perform the division to determine the Y correction, scanning continues with the Y correction being applied after the next scan. If a correction is required in X, the magnitude of the correction is 1, which is applied before the next scan begins After an alignment correction occurs, the accumulator must be reinitialized to a negative value. If it is not, the alignment error may be overcorrected by the time the accumulator returns to a negative value. The accumulator is reinitialized by setting it equal to one quarter of the value of its negative accumulator, and the negative accumulator is reinitialized to three quarters of its old value. This permits alignment correction to be performed more readily in the direction of the last correction.

Figure 15A:
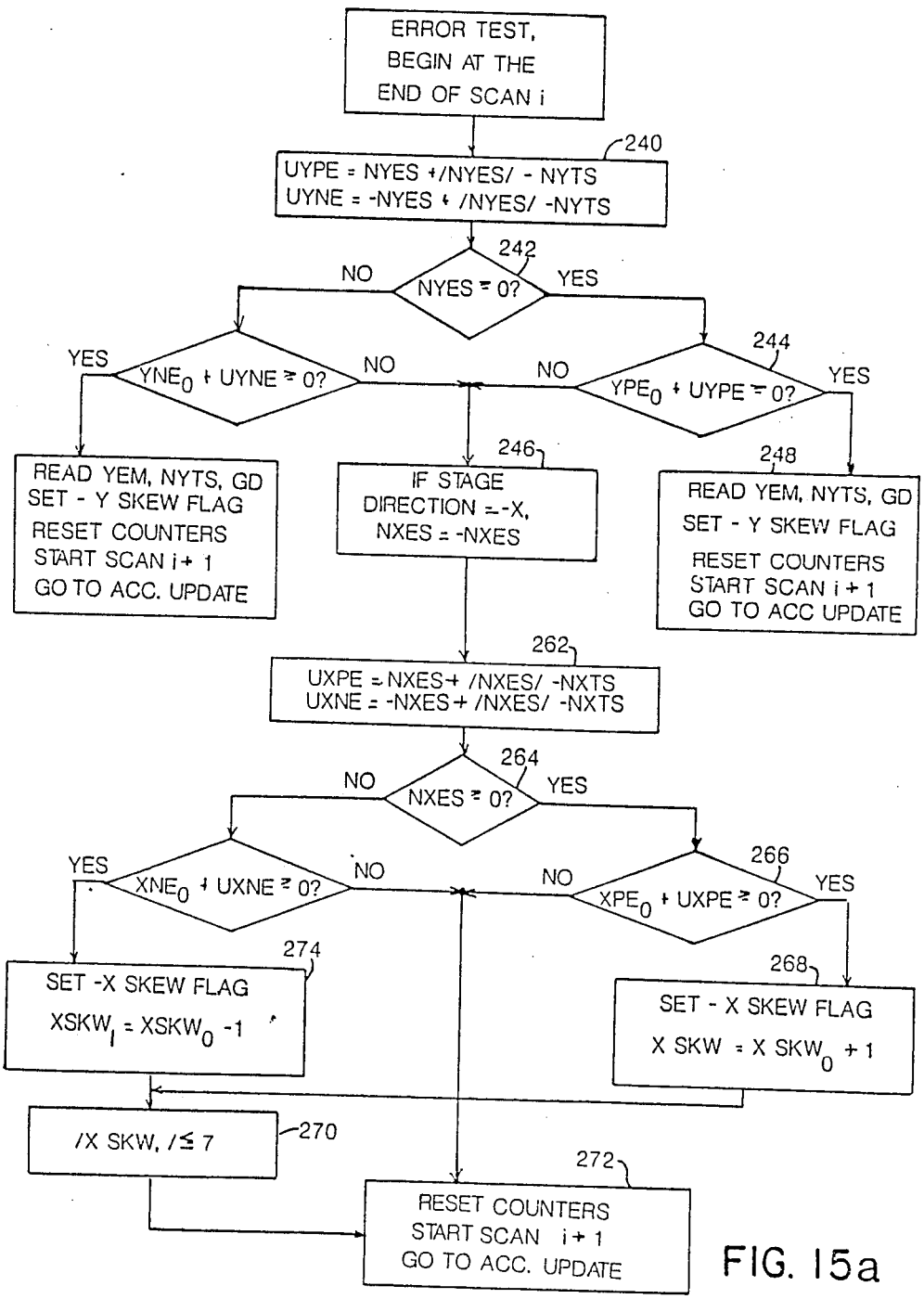
FIGS. 15a and 15b are a flow chart of the computational branches of the alignment processor circuit.
Figure 15B:
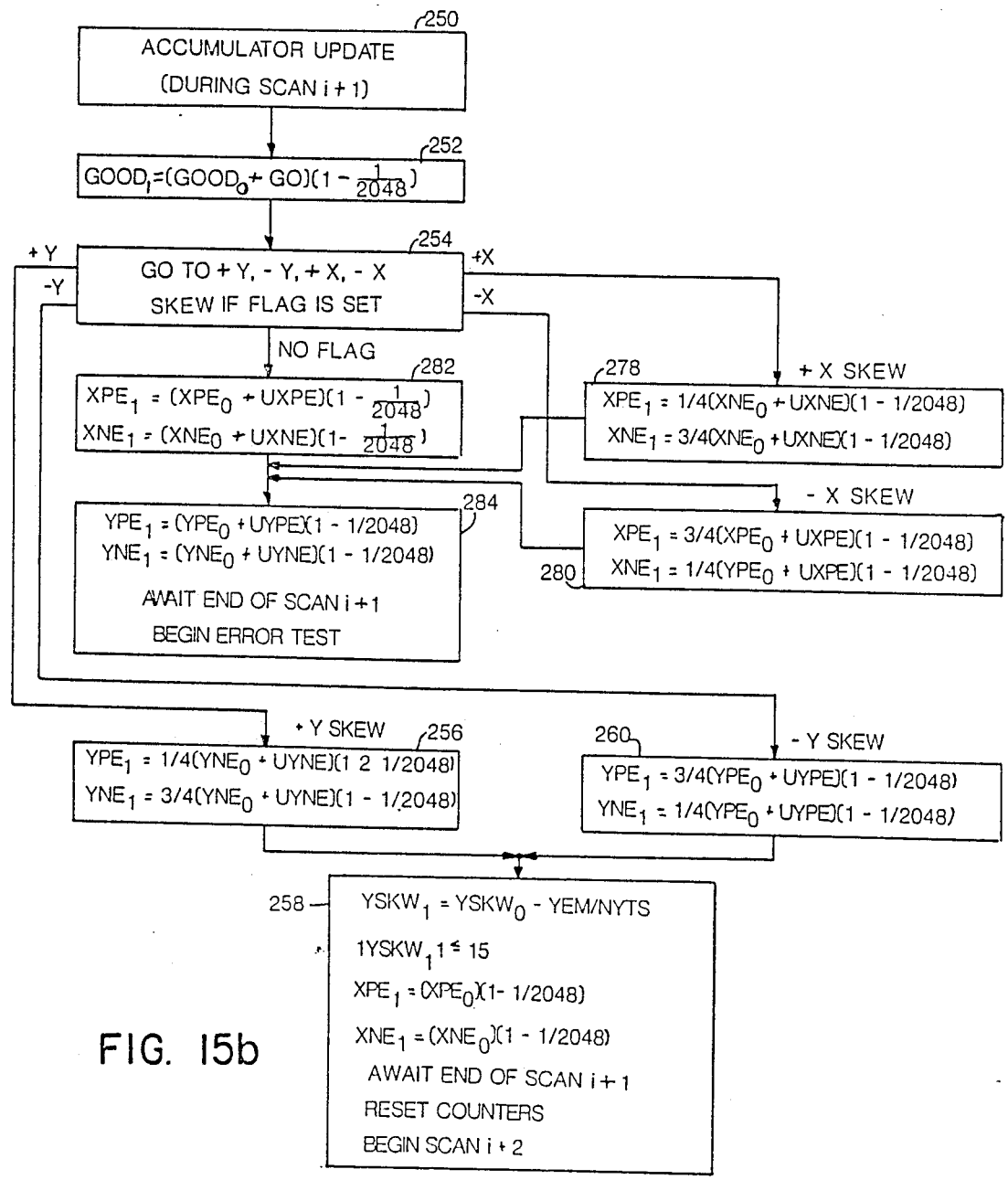

FIGS. 15a and 15b are flow diagrams which specifically describe the operation of the alignment processor 186. After the end of a scan, the X and Y counters 194, 196, 198, 224, and 226 contain the net error and total sample results obtained during the scan. First, the Y accumulator updates are calculated, UYPE and UYNE, as shown in block 240. UYPE, for example, equals NYES plus the absolute value of NYES plus NYTS. Next, the flow branches at 242, according to the sense of NYES. If UYPE is greater than zero, then a significant number of positive errors were just found. However, UYPE must be added to the accumulated value first in order to determine whether the error is significant in light of past errors. This test is performed at 244 and if the sum is still negative, the flow passes into an X calculation at 246. If the sum tested at 244 is positive, then a positive Y alignment correction is required, block 248. If so, YEM, NYTS, and GD are read from their counters and stored for later calculations. Also, a +Y skew flag is set for later use in branching, the X and Y counters are reset and the next scan is begun.

After the next scan has begun, the accumulators are updated at 250. First the GOOD accumulator is updated at 252 by adding GD to the current value $GOOD_0$ and then multiplying by the exponential decay factor. The product is then restored in the accumulator as $GOOD_1$. Next, the flow branches at 254 according to previously set flags. In this example, the +Y skew flag was set, so the flow branches to block 256, where the YPE and YNE accumulators are updated. The current value of the YNE accumulator, YNEQ, is added to UYNE and is decayed by the decay factor. One quarter of the product is stored in YPE and three quarters is stored in YNE. The flow then continues to block 258, where the Y offset, YSKW, is calculated. The current value of the Y offset, $YSKW_0$, is read by the alignment processor from the memory address control 132 and YEM/NYTS is subtracted from it to yield the updated offset $YSKW_1$. $YSKW_1$ is then checked to verify that it does not exceed a maximum value. The memory address control will use $YSKW_1$ to reposition the inspection windows for the next scan. Next, the XPE and XNE accumulators are decayed by the decay factor, and at the end of the scan, the Y and X counters are reset to begin the next scan. Note that since the Y alignment correction took two scans to accomplish, the data in the counters at the end of the second scan is discarded.

A similar calculational path would be followed when NYES is negative and the accumulated YNE value permits a −Y alignment correction. The only effective difference between these calculational paths is at block 260 where the YPE and YNE accumulators are reinitialized as a function of YPE.

If the Y alignment error is not significant enough to warrant correction, the flow transfers to the X calculation at 246. First the stage direction is accommodated by reversing the sense of NXES if the stage is moving in the −X direction. Then, UXPE and UXNE are calculated at 262, and the flow divides to positive and negative error branches at 264. On the positive branch, the significance of the accumulated plus updated errors is tested against zero at 266. If the error is significant, a +X skew flag is set at 268. Also the X offset, XSKW, is incremented by 1. Next, XSKW is tested and clamped to a maximum value if the magnitude exceeds 7 at block 270. At this point, 272, the updates necessary for the next scan have been completed, so the X and Y counters are reset and the next scan begins. All branches of the X calculation reaches the final block 272. If a negative correction has been required, the −X skew flag would have been set, XSKW reduced by block 274.

The accumulators are updated during the next scan regardless of whether or not an alignment correction occurred. As mentioned above, the GOOD accumulator is updated and decayed at 252 and the flow branches at 254. If either the +X or −X skew flag was set, the flow branches to 278 or 280 to reinitialize XPE and XNE. If no flags were set, XPE is updated by UXPE and decayed by the decay factor, and XNE is updated by UXNE and decayed by the decay factor, all at block 282. Next, assuming that the Y skew flags were not set, YPE and YNE are updated by UYPE and UYNE, respectively, and decayed by the decay factor, at 284. This concludes the accumulator updates. The alignment processor awaits the end of the current scan to begin the next error updates.

At the end of each scan, the value of XSKW is checked by a comparator and if the magnitude is greater than 1, the signal EXCESS is set true, and the stage direction and XSKW sign is reflected in the EXDIR signal. These signals are used by the system timing control as described below.

Figure 16:
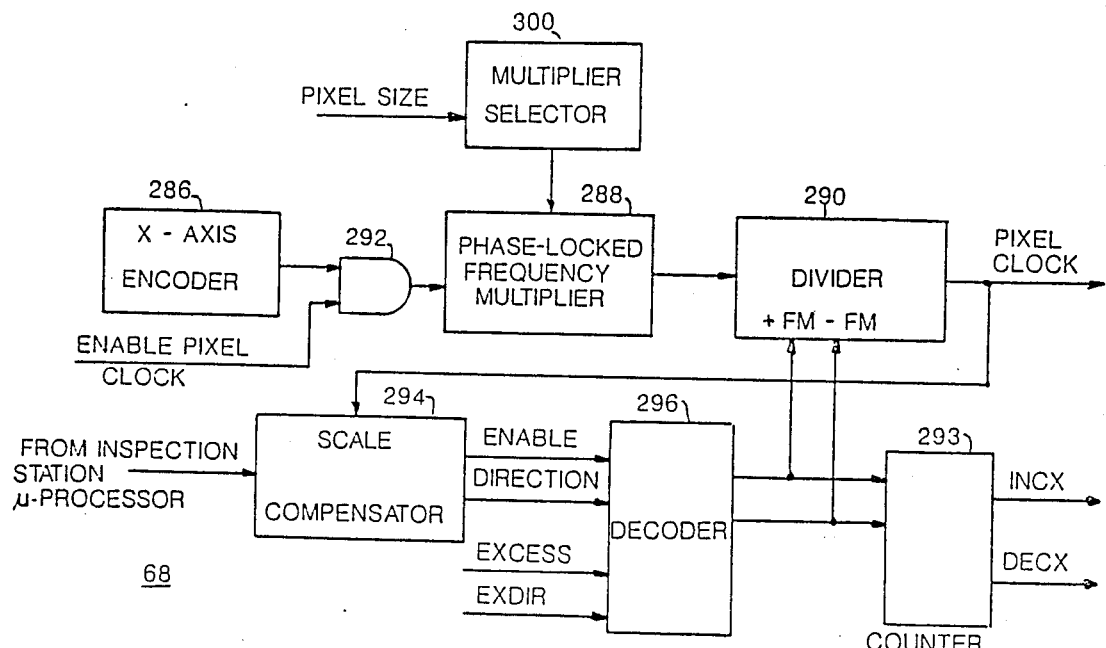
FIG. 16 is a functional block diagram of a system timing control circuit utilized by the reticle inspection system of FIG. 1.

Moving now to FIG. 16, a portion of the system timing control 68, that modulates the X-dimension of the pixels to extend the range of X alignment correction by correcting slow moving alignment errors, is illustrated. In standard operation, the system timing control converts encoder clock pulses from the X axis encoder 286 into the pixel clock by multiplying the encoder clock with a multiplier 288 and by dividing the resultant by a divider 290. The enable pixel clock signal, described above in relation to FIGS. 5 and 6, is combined with the encoder clock by an AND gate 292 to control the generation of the pixel clock.

If there is an overall average X alignment error between the optical and database representations of the reticle during a portion of a swath, the X-dimension of the optical pixel can be modulated by the system timing control to correct the error. If, for example, the database representation were on the average, leading the optical representation, slightly larger optical pixels would allow the optical representation to catch up to the database over many sensor scans. To expand the pixel size in X, a slightly slower pixel clock frequency is used so that the stage travels slightly farther between scans. Care must be taken not to overly modulate the pixel size because it could adversely affect the measurements made by the photosensors which integrate the incident light over the period of one sensor scan. This correction technique can be used to correct slow moving mis-registration errors by effecting a slow moving alignment change.

The alignment correction subsystem informs the system timing control whether a correction is needed (EXCESS) and in which direction (EXDIR). Alternatively, a scale compensator 294 may be utilized to direct the pixel modulation process. When the inspection station 22 is first calibrated, the encoder clock signals and the optical representation of the reticle can be sent to the reticle inspection adapter 26 for comparison against the database. At that time, calibration factors are computed and stored. Those calibration factors are used by the scale-compensator to selectively modulate the X pixel size to cancel scale type errors. A decoder 296 combines the scale compensator and the alignment corrections and relays the result to the divider 290. To modulate the pixel clock frequency, divider 290 divides by a slightly larger or smaller number according to whether the +FM or −FM line is enabled. A counter 298 counts the number of scans in which the pixel clock is modulated. When the pixel modulation has accumulated to the point where one full pixel has been added or subtracted, the counter informs the memory address control 132 via signals INCX or DECX.

Occasionally a faster inspection time at a lower resolution is needed. This may occur, for example, when a 10× reticle is inspected, and small defects may be ignored. To accomplish a faster inspection at lower resolution, two things must happen: (1) The stage must be moved at twice the normal speed to increase the pixel size in X; and (2) adjacent pixels in Y must be combined to enlarge the resultant Y-pixels. When the stage speed is doubled, the multiplying factor of multiplier 288 is halved to retain the same pixel clock frequency. A multiplier selector 300 instructs the multiplier as to which multiplying factor to use.

Figure 17:
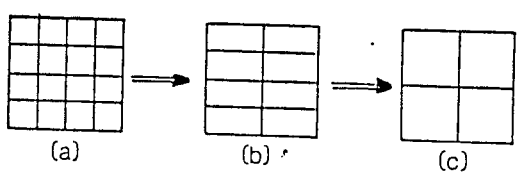
FIG. 17 is a diagram that illustrates the procedure of mapping pixels for image compression.
Figure 18:
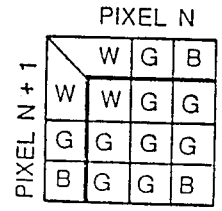
FIG. 18 is a logical truth table used in combining pixels for image compression.

FIG. 17 depicts the mapping process. The standard pixel configuration is shown at (a). By doubling the stage speed and holding the pixel clock constant, the rectangular pixels of (b) result. Adjacent rectangular pixels are combined according to the chart of FIG. 18, resulting in the large square pixels of (c).

Finally, it should be noted that the reticle inspection system has been designed so that the inspection station 22 in FIG. 1 can be operated as a stand-alone, die-to-die, comparison system. Later upgrade to die-to-database comparison can be accomplished by adding a reticle inspection adapter to the existing inspection station. This upgrade still preserves the ability of the inspection station to inspect in a die-to-die mode.

Although the present invention has been described above in terms of a preferred embodiment specifically designed to test reticles, it will be understood that the system or various parts thereof could be adapted for other applications. Accordingly, it is Applicants' intent that the appended claims be interpreted as covering all such alternations, modifications or other applications as fall within the true scope of the invention.

What is claimed is:

1. Optical inspection apparatus for scanning a patterned object and comparing it to information contained in an electronic data base, comprising:
   optical scanning means responsive to a first timing control signal and operative to scan the patterned object and to develop a first data signal including a sampled and quantitized electronic representation of the patterned object;
   data base means responsive to a second timing control signal and operative to generate a second data signal corresponding to a design database description of the patterned object scanning by said scanning means, said second data signal having a variable time relationship to said first data signal;
   data alignment means for comparing said first data signal to said second data signal and for developing an excess alignment signal which corresponds to any misalignment of said second data signal exceeding a predetermined limit, and for adjusting said time relationship between said first data signal and said second data signal to provide aligned first and second data signals which are time coincident with each other;
   timing control means responsive to said excess alignment signal and operative to develop said first and second timing control signals, said first and second timing control signals being used to adjust the relative output data signal rates of said optical scanning means and said data base means for the purpose of maintaining the alignment of said first and second data signals within predetermined limits; and
   defect detector means for comparing said aligned first data signal and said aligned second data signal and for developing defect data signals corresponding to differences therebetween having predetermined characteristics.

2. Optical inspection apparatus as recited in claim 1 wherein said database means includes:
   electronic storage means for storing said design database description;
   pattern memory means for receiving a selected portion of said design database description stored in said storage means;
   pattern generating means for converting said selected portion into bit mapped data;
   bit map memory means for storing said bit mapped data; and
   scan converter means for converting the stored bit mapped data into said second data signal.

3. Optical inspection apparatus as recited in claim 2 wherein said pattern memory means is a double-buffered memory and said bit map memory is a double-buffered memory.

4. Optical inspection apparatus as recited in claim 3 wherein said data alignment means includes:
   an alignment memory for receiving and storing said first and second data signals and for responding to alignment error correction signals to develop said aligned first and second data signals; and
   alignment error detection means for comparing portions of said first and second data signals stored in said alignment memory and developing said alignment error correction signals.

5. Optical inspection apparatus as recited in claim 4 wherein said alignment memory includes:
   a memory address control means responsive to said alignment error correction signal and operative to develop first and second data select signals;
   a left pixel memory for storing a quantity of said first data signal and responsive to said first data select signal to output a portion thereof as said aligned first data signal; and
   a right pixel memory for storing a quantity of said second data signal and responsive to said second data select signal to output a portion thereof as said aligned second data signal.

6. Optical inspection apparatus as recited in claim 4 wherein said alignment error detection means includes:
   two-dimensional phase detection means which compares portions of said first and second data signals and develops error signals corresponding to the instantaneous magnitude and direction of misalignment therebetween; and
   alignment processor means responsive to said error signals and operative to generate said alignment error correction signals and said excess alignment signal.

7. Optical inspection apparatus as recited in claim 6 wherein said two-dimensional phase detection means includes:
   X-direction error detection means responsive to portions of said first and second data signals and operative to generate X-components of said error signals; and
   Y-direction error detection means responsive to portions of said first and second data signals and operative to generate Y-components of said error signals.

8. Optical inspection apparatus as recited in claim 6 wherein said alignment error detection means further includes goodness logic means responsive to portions of said first and second data signals and operative to generate goodness signals qualifying said error signals for input to said alignment processor means.

9. Optical inspection apparatus as recited in claim 4 wherein said timing control means includes a controllable phase locked oscillator means responsive to a scan position signal developed by said optical sensing means and to said excess alignment signal and operative to generate said first and second timing control signals.

10. Optical inspection apparatus as recited in claim 9 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

11. Optical inspection apparatus as recited in claim 9 wherein said timing control means further includes a scale compensation means for generating a scale compensation signal, and wherein said phase locked oscillator means is further responsive to said scale compensation signal and operative to modify at least one of said first and second timing signals to compensate for known scale errors in the patterned object.

12. Optical inspection apparatus as recited in claim 11 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

13. Optical inspection apparatus as recited in claim 3 wherein said timing control means includes a controllable phase locked oscillator means responsive to a scan position signal developed by said optical sensing means and to said excess alignment signal and operative to generate said first and second timing control signals.

14. Optical inspection apparatus as recited in claim 13 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

15. Optical inspection apparatus as recited in claim 13 wherein said timing control means further includes a scale compensation means for generating a scale compensation signal, and wherein said phase locked oscillator means is further responsive to said scale compensation signal and operative to modify at least one of said first and second timing signals to compensate for known scale errors in the patterned object.

16. Optical inspection apparatus as recited in claim 15 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

17. Optical inspection apparatus as recited in claim 2 wherein said data alignment means includes:
   an alignment memory for receiving and storing said first and second data signals and for responding to alignment error correction signals to develop said aligned first and second data signals; and
   alignment error detection means for comparing portions of said first and second data signals stored in said alignment memory and developing said alignment error correction signals.

18. Optical inspection apparatus as recited in claim 17 wherein said alignment memory includes:
   a memory address control means responsive to said alignment error correction signal and operative to develop first and second data select signals;
   a left pixel memory for storing a quantity of said first data signal and responsive to said first data select signal to output a portion thereof as said aligned first data signal; and
   a right pixel memory for storing a quantity of said second data signal and responsive to said second data select signal to output a portion thereof as said aligned second data signal.

19. Optical inspection apparatus as recited in claim 17 wherein said alignment error detection means includes:
   two-dimensional phase detection means which compares portions of said first and second data signals and develops error signals corresponding to the instantaneous magnitude and direction of misalignment therebetween; and
   alignment processor means responsive to said error signals and operative to generate said alignment error correction signals and said excess alignment signal.

20. Optical inspection apparatus as recited in claim 19 wherein said two-dimensional phase detection means includes:
   x-direction error detection means responsive to portions of said first and second data signals and operative to generate X-components of said error signals; and
   y-direction error detection means responsive to portions of said first and second data signals and operative to generate Y-components of said error signals.

21. Optical inspection apparatus as recited in claim 19 wherein said alignment error detection means further includes goodness logic means responsive to portions of said first and second data signals and operative to generate goodness signals qualifying said error signals for input to said alignment processor means.

22. Optical inspection apparatus as recited in claim 17 wherein said timing control means includes a controllable phase locked oscillator means responsive to a scan position signal developed by said optical sensing means and to said excess alignment signal and operative to generate said first and second timing control signals.

23. Optical inspection apparatus as recited in claim 22 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

24. Optical inspection apparatus as recited in claim 22 wherein said timing control means further includes a scale compensation means for generating a scale compensation signal, and wherein said phase locked oscillator means is further responsive to said scale compensation signal and operative to modify at least one of said first and second timing signals to compensate for known scale errors in the patterned object.

25. Optical inspection apparatus as recited in claim 24 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

26. Optical inspection apparatus as recited in claim 2 wherein said timing control means includes a controllable phase locked oscillator means responsive to a scan position signal developed by said optical sensing means and to said excess alignment signal and operative to generate said first and second timing control signals.

27. Optical inspection apparatus as recited in claim 26 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

28. Optical inspection apparatus as recited in claim 26 wherein said timing control means further includes a scale compensation means for generating a scale compensation signal, and wherein said phase locked oscillator means is further responsive to said scale compensation signal and operative to modify at least one of said first and second timing signals to compensate for known scale errors in the patterned object.

29. Optical inspection apparatus as recited in claim 28 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

30. Optical inspection apparatus as recited in claim 1 wherein said data alignment means includes:
an alignment memory for receiving and storing said first and second data signals and for responding to alignment error correction signals to develop said aligned first and second data signals; and
alignment error detection means for comparing portions of said first and second data signals stored in said alignment memory and developing said alignment error corresponding signals.

31. Optical inspection apparatus as recited in claim 30 wherein said alignment memory includes:

a memory address control means responsive to said alignment error correction signal and operative to develop first and second data select signals;
a left pixel memory for storing a quantity of said first data signal and responsive to said first data select signal to output a portion thereof as said aligned first data signal; and
a right pixel memory for storing a quantity of said second data signal and responsive to said second data select signal to output a portion thereof as said aligned second data signal.

32. Optical inspection apparatus as recited in claim 30 wherein said alignment error detection means includes:
two-dimensional phase detection means which compares portions of said first and second data signals and develops error signals corresponding to the phase instantaneous magnitude and direction of misalignment therebetween; and
alignment processor means responsive to said error signals and operative to generate said alignment error correction signals and said excess alignment signal.

33. Optical inspection apparatus as recited in claim 32 wherein said two-dimensional phase detection means includes:
X-direction error detection means responsive to portions of said first and second data signals and operative to generate X-components of said error signals; and
Y-direction error detection means responsive to portions of said first and second data signals and operative to generate Y-components of said error signals.

34. Optical inspection apparatus as recited in claim 32 wherein said alignment error detection means further includes goodness logic means responsive to portions of said first and second data signals and operative to generate goodness signals qualifying said error signals for input to said alignment processor means.

35. Optical inspection apparatus as recited in claim 30 wherein said timing control means includes a controllable phase locked oscillator means responsive to a scan position signal developed by said optical sensing means and to said excess alignment signal and operative to generate said first and second timing control signals.

36. Optical inspection apparatus as recited in claim 35 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

37. Optical inspection apparatus as recited in claim 35 wherein said timing control means further includes a scale compensation means for generating a scale compensation signal, and wherein said phase locked oscillator means is further responsive to said scale compensation signal and operative to modify at least one of said first and second timing signals to compensate for known scale errors in the patterned object.

38. Optical inspection apparatus as recited in claim 37 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

39. Optical inspection apparatus as recited in claim 1 wherein said timing control means includes a controllable phase locked oscillator means responsive to a scan position signal developing by said optical sensing means and to said excess alignment signal and operative to generate said first and second timing control signals.

40. Optical inspection apparatus as recited in claim 39 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

41. Optical inspection apparatus as recited in claim 39 wherein said timing control means further includes a scale compensation means for generating a scale compensation signal, and wherein said phase locked oscillator means is further responsive to said scale compensation signal and operative to modify at least one of said first and second timing signals to compensate for known scale errors in the patterned object.

42. Optical inspection apparatus as recited in claim 41 wherein said timing control means is further responsive to an input pixel size select signal developed by said optical scanning means and operative to modify certain characteristics of said first and second timing control signals so as to cause said optical scanning means to scan at a speed such that it has a resolution corresponding to said input pixel size select signal, and operative to cause said database means to generate said second data signal at a resolution likewise corresponding to said input pixel size select signal.

* * * * *